US006642002B2

(12) United States Patent
Loyd et al.

(10) Patent No.: US 6,642,002 B2
(45) Date of Patent: Nov. 4, 2003

(54) METHOD OF DIAGNOSING PULMONARY HYPERTENSION

(75) Inventors: James E. Loyd, Nashville, TN (US); Kirk B. Lane, Brentwood, TN (US); John A. Phillips, III, Brentwood, TN (US); Richard C. Trembath, Rutland (GB); Rajiv D. Machado, Leicester (GB); Jennifer R. Thomson, Leeds (GB); William C. Nichols, Loveland, OH (US); Michael W. Pauciulo, Blue Ash, OH (US); Tatiana Foroud, Indianapolis, IN (US)

(73) Assignees: Vanderbilt University, Nashville, TN (US); Advanced Research & Technology Institute, Indianapolis, ID (US); Children's Hospital Medical Center, Cincinnati, OH (US); University of Leicester, Leicester (GB)

( * ) Notice: Subject to any disclaimer, the term of this patent is extended or adjusted under 35 U.S.C. 154(b) by 0 days.

(21) Appl. No.: 09/908,500

(22) Filed: Jul. 17, 2001

(65) Prior Publication Data

US 2002/0102576 A1 Aug. 1, 2002

Related U.S. Application Data

(60) Provisional application No. 60/218,740, filed on Jul. 17, 2000, and provisional application No. 60/220,133, filed on Jul. 21, 2000.

(51) Int. Cl.[7] .......................... C12Q 1/68; C12P 19/34; C07H 21/02; C07H 21/04

(52) U.S. Cl. ..................... 435/6; 435/91.2; 536/23.5; 536/24.31; 536/24.33

(58) Field of Search ................... 435/6, 91.2; 536/23.5, 536/24.31, 24.33

(56) References Cited

U.S. PATENT DOCUMENTS

| 3,610,795 A | 10/1971 | Antoine ........................... 13/9 |
| 2002/0002229 A1 * | 1/2002 | Morse et al. ................... 435/6 |

FOREIGN PATENT DOCUMENTS

| WO | WO 02/04684 A1 | 1/2002 |
| WO | WO 02/16398 A2 | 2/2002 |

OTHER PUBLICATIONS

Deng et al. American Journal of Human Genetics. Sep. 2000. 67: 737–744.*
Machado et al. American Journal of Human Genetics. Jan. 2001. 68: 92–101.*
Deng et al., Familial Primary Pulmonary Hypertension (Gene PPH1) Is Caused by Mutations in the Bone Morphogenetic Protein Receptor–II Gene, *Am. J. Hum. Genet.* 67:737–744 (2000).
Lane et al., Heterozygous germline mutations in BMPR2, encoding a TGF–β receptor, cause familial primary pulmonary hypertension, *Nature Genetics*, vol. 26:81–84 (Sep. 2000). XP002907136.
Machado et al., BMPR2 Haploinsufficiency as the Inherited Molecular Mechanism for primary Pulmonary Hypertension, *American Journal of Human Genetics*, 68:92–102 (2001). XP002909517.
Thomson et al., Sporadic primary pulmonary hypertension is associated with germline mutations of the gene encoding BMPR–II, a receptor member of the TGF–β family, *J. Med. Genet.* 37:741–745 (2000). XP001118640.
Abenhaim et al. Appetite–Suppressant Drugs and the Risk of Pulmonary Hypertension. *N. Eng. J. MEd.* 335(9):609–616 (1996).
Agrawal et al. Cell–Cycle kinetics and VSV–G pseudotyped retrovirus–mediated gene transfer in blood–derived $CD34^+$ cells. *Exper. Hematol.* 24:738–747 (1996).
Alvarez et al. A Phase I Study of Recombinant Adenovirus Vector–Mediated Intraperitoneal Delivery of Herpes Simplex Virus Thymidine Kinase (HSV–TK) Gene and Intravenous Genciclovir for Previously Treated Ovarian and Extraovarian Cancer Patients. *Hum. Gene Ther.* 8:597–613 (1997).
Ashmore et al. Paradoxical constriction to platelets by arteries from rats with pulmonary hypertension. *Am. J. Physiol.* (6 Pt 2):H9129–H1934 (1991).
Beppu et al. cDNA Cloning and Gemomic Organization of the Mouse BMP Type II Receptor. *Biochem. Biophys. Res. Comm.* 235:499–504 (1997).
Blobe et al. Role of Transforming Growth Factor β in Human Disease. *N. Eng. J. Med.* 342(18):1350–1358 (2000).
Botney et al. Vascular Remodeling in Primary Pulmonary Hypertension: Potential Role for Transforming Growth Factor–β. *Am. J. Pathol.* 144(2):286–295 (1994).
Carcamo et al. Disruption of Transforming Growth Factor β Signaling by a Mutation That Prevents Transphosporylation within the Receptor Complex. *Mol. Cell. Biol.* 15(3):1573–1581 (1995).
Crystal. Phase I Study of Direct Administration of a Replication Deficient Adenovirus Vector Containing E–coli Cytosine Deaminase Gene to Metastatic Colon Carcinoma of the Liver in Association with the Oral Administration of the Pro–Drug5–Fluorocytosine. *Hum. Gene Ther.* 8:985–1001 (1997).

(List continued on next page.)

*Primary Examiner*—Carla J. Myers
(74) *Attorney, Agent, or Firm*—Needle & Rosenberg, P.C.

(57) ABSTRACT

This invention relates generally to a method of identifying an individual having an increased susceptibility to developing Familial Primary Pulmonary Hypertension (FPPH), as well as to a method for diagnosing an individual suffering from FPPH. The invention also relates to a method of identifying an individual having an increased susceptibility to developing (non-familial) Primary Pulmonary Hypertension (PPH), as well as to a method for diagnosing an individual suffering from PPH.

4 Claims, 4 Drawing Sheets

OTHER PUBLICATIONS

Deng et al. Fine Mapping of PPH1, a Gene for Familial Primary Pulmonary Hypertension, to a 3–cM Region on Chromosome 2q33. *Am. J. Res. & Crit. Care Med.* 160:1055–1059 (2000).

Elliott et al. Coancestry in Apparently Sporadic Primary Pulmonary Hypertension. *Chest* 108(4):973–977 (1995).

Gaine and Rubin. Primary pulmonary hypertension. *Lancet* 352:719–725 (1998).

Gilboa et al. Bone Morphogentic Protein Receptor Complexes on the Surface of Live Cells: A New Oligomerization Mode for Serine/Theromine Kinase Receptors, *Mol. Biol. Cell.* 11:1023–1035 (2000).

Gomez–Sanchez et al. Clinical and Pathologic Manifestations of Pulmonary Vascular Disease in the Toxic Oil Syndrome. *J. Am. Coll. Card.* 18(6):1539–1545 (1991).

Gonzalez et al. Pulmonary hypertension, family, and environment. *J. Hum. Hyperten.* 11(9):559–561 (1997).

Gonzalez et al. The Pulmonary Hypertensive Fawn–hooded Rat Has a Normal Serotonin Transporter Coding Sequence. *Am. J. Res Cell & Mol. Biol.* 19(2):245–249 (1998).

Goodman et al. Recombinant Adeno–Associated Virus–Mediated Gene Transfer Into Hematopoiatic Progenitor Cells. *Blood* 84(5):1492–1500 (1994).

Gust et al. Vascular remodeling in experimentally induced subacute canine pulmonary hypertension. *Exp. Lung Res.* 27(1):1–12 (2000).

Hadano et al. A yeast artifical chromosome–based physical map of the juvenile amyotrophic lateral sclerosis (ALS2) critical region of human chromosome 2q33–q34. *Gene* 55:106–112 (1999).

The International PPH Consortium et al.. Heterozygous germline mutations in BMPR2, encoding a TGF–β receptor, cause of familial primary pulmonary hypertension. *Nat. Gen.* 26:81–84 (2000).

Ito et al. Alterations of endothelium and smooth muscle function in monocrotaline–induced pulmonary hypertensive arteries. *Am. J. Physiol.Heart Circ. Physiol.* 279(4):H1786–H1795 (2000).

Johnson et al. Pulmonary Veins and Bronchial Vessels Undergo Remodeling in Sustained Pulmonary Hypertension Induce by Continuous Air Embolization into Sheep. *Exp. Lung Res.* 23(5):459–473 (1997).

Kameji et al. Increase of collagen synthesis in pulmonary arteries of monocrotaline–treated rats. *Experientia* 36(4):441–442 (1980).

Kawabata et al. Cloning of a Novel Type II Serine/Threonine Kinse Receptor through Interaction with Type I Transforming Growth Factor–β Receptor. *J. Biol. Chem.* 270(10):5625–5930 (1995).

Le Cras et al. Abnormal lung growth and the development of pulmonary hypertension in the Fawn–Hooded rat. *Am. J. Physiol.* 277(4 Pt 10):L409–L718 (1999).

Le Cras et al. Early abnormalities of pulmonary vascular development in the Fawn–Hooded rat raised at Denver's altitude. *Am. J. Physiol. Lung Cell. Mol. Physiol.* 279(2):L283–L291 (2000).

Lee et al. Monoclonal endothelial cell proliferation is present in primary by not secondary pulmonary hypertension: clinical patterns. *J. Clin. Invest.* 101(5):927–934 (1998).

Loyd et al. Heterogeneity of Pathologic Lesions in Familial Primary Pulmonary Hypertension. *Am. Rev. Res. Dis.* 138:952–957 (1988).

Loyd et al. Familial Primary Pulmonary Hypertension: Clinical Patterns. *Am. Rev. Res. Dis.* 129:134–197 (1984).

Lu et al. HNPCC associated with germline mutation in the TGF–β type II receptor gene. *Nat. Gen.* 19:17–18 (May 1998).

Lui et al. Human Type II Receptor for Bone Morphogenic Proteins (BMPs): Extension of the Two Kinase Receptor Model to the BMPs. *Mol. Cell. Biol.* 15(7):3479–3486 (1995).

Machado et al. A physical and transcript map based upon refinement of the critical interval for PPHq, a gene for familiar primary pulmonary hypertension. *Gene.* 68:220–228 (2000).

Maisel et al. Pertussis Toxin Treatment of Whole Blood: A Novel Approach to Assess G Protein Function in Congestive Heart Failure. *Circulation* 81(4–6):1161–2075 (1990).

Marchuk. Genetic abnormalities in hereditary hemorrhagic telangiectasia. *Curr. Opin. Hematol* 5:332–338 (1998).

Massague and Cheng. Controlling TGF–β signaling. *Genes Dev.* 14:627–644 (2000).

Mesa et al. Human Immunodeficiency Virus Infection and Pulmonary Hypertension: Two New Cases and a Review of 86 Reported Cases. *Mayo Clinic Proceedings* 73:37:37–45 (1998).

Miller Buttimore. Redesign of Retrovirus Packaging Cell Lines To Avoid Recombination Leading to Helper Virus Production. *Mol. Cell. Biol.* 6(8):2895–2902 (1986).

Mitani et al. Transduction of Human Bone Marrow by Adenoviral Vector. *Hum. Gene Ther.* 5:941–948 (1994).

Morio et al. Distal Airspace Enlargement in the Fawn–Hooded Rat: Influences of Aging and Aleolar Wall Destruction. *Respiration* 68(1):78–86 (2001).

Morrell et al. Angiotensin II activates MAPK and stimulates growth of human pulmonary artery smooth muscle via AT, receptors. *Am. J. Physiol.* 277:L440–L448 (1999).

Morse et al. Mapping of Familiar Pulmonary Hypertension Locus (PPH1) to Chromosome 2q31–q32. *Circulation* 95(12):2603–2606 (1997).

Nagaya et al. Gene Transfer of Human Prostacyclin Synthase Ameliorates Monocrotaline–Induced Pulmonary Hypertension in Rats. *Circulation* 102(16):2005–2010 (2000).

Naldini et al. In Vivo Gene Delivery and Stable Transduction of Nondividing Cells by a Lentiviral Vector. *Science* 272:263–267 (1996).

Narayanaswamy et al. Animal models for Atherosclerosis, Restenosis, and Endovascular Graft Research. *J. Vasc. Interv. Radiol.* 11:5–17 (2000).

Nichols et al. Localization of the gene for familial primary pulmonary hypertension to chromosome 2q31–32. *Nat. Gen.* 15:277–280 (1997).

Pastan et al. A retrovirus carrying and MDR1 cDNA confers multidrug resistence and polarized expressin of P–glycoprotein in MDCK cells. *Proc. Natl. Acad. Sci. USA* 85:4486–4490 (1988).

Perkett et al. Continuous air embolization into sheep causes sustained pulmonary hypertension and increased pulmonary vasoreactivity. *Am. J. Path.* 132(3):444–454 (1988).

Perkett et al. Expression of Transformation Growth Factor–β mRNAs and Protein in Pulmonary Vascular Remodeling in the Sheep Air Embolization Model of Pulmonary Hypertension. *Am. J. Respir. Cell Mol. Biol.* 11(1):16–24 (1994).

Perkett et al. Insulin–like Growth Factor I and Pulmonary Hypertension Induced by Continuous Air Embolization in Sheep. *Am. J. Respir. Mol. Biol.* 6(1):82–87 (1992).

Perkett et al. Sequence and Structural Changes and Elastin Peptide Release During Vascular Remodeling in Sheep with Chronic Pulmonary Hypertension Induced by Air Embolization. *Am. J. Pathol.* 139(6):1319–1329 (Dec. 1991).

Pietra et al. Histopathology of primary pulmonary hypertension. A qualitative and quantitative of pulmonary blood vessels from 58 patients in the National Heart, Lung, and Blood Institute, Primary Hypertension Registry. *Circulation* 80:1198–1209 (1989).

Poernama et al. High Density Lipoprotein Deficiency Syndrome in Chickens is not with an Icreased Susceptibility to Atheroclerosis. *Arterioscler. Thromb.* 12:601–607 (1992).

Provoost. Spontaneous glomerulosclerosis: Insights from the fawn–hooded rat. *Kidney International* 45 (suppl.45):S2–S5 (1994).

Rich et al. Primary Pulmonary Hypertension: A National Prospective Study. *Ann. Intern. Med.* 107:216–223 (1987).

Rosenzweig et al. Cloning and characterization of a human type II receptor for bone morphogenetic proteins. *Proc. Natl. Acad. Sci. U.S.A.* 92:7632–7636 (1995).

Rubin. ACCP Consensus Statment: Primary Pulmonary Hypertension. *Chest.* 104(1):236–250 (1993).

Rubin. Primary Pulmonary Hypertension. *N. Eng. J. Med.* 336(2):111–117 (1997).

Sato et al. Factors Influencing the Idiopathic Development of Pulmonary Hypertension in the Fawn Hooded Rat. *Am. Rev. Res. Dis.* 145(4 Pt. 1):793–797 (1992).

Schreyer et al. Hypercatabolism of Lipoprotein–Free Apolipoprotein A–I in HDL–Deficient Mutant Chickens. *Arteriscler. Thromb.* 14:2053–2059 (1994).

Schwartzenberger et al. Targeted Gene Transfer to Human Hematopoitic Progenitor Cell Lines Through the c–kit Receptor. *Blood* 87(2):472–478 (1996).

Shackleton et al. *LMNA*, encoding lamin A/C, is mutated in partial lipodystrophy. *Nat. Gen.* 24:153–156 (2000).

Shubat et al. Pulmonary Vascular Responses Induced by the Pyrrolizidine Alkaliod, Monocrotaline, in Rats. *Toxicon.* 25(9):995–1002 (1987).

Smith. Mouse Models of Atherosclerosis. *Lab. Anim. Sci.* 48(6):573–579 (1998).

Tanabe et al. Experimental study on monocrotaline induced pulmonary hypertensive rats. (1) Effects of long–term injection of immunosuppressant. *Tokai J. Exp. & Clinic. Med.* 6(1):41–48 (1981).

Wilkie. The molecular basis of genetic dominance. *J. Med. Genet.* 31:89–98 (1994).

Wrana et al. Two Distinct Transmembrane Serine/Threonine Kinases from Drosophila melanogaster Form an Activin Receptor Complex. *Mol. Cell. Biol.* 14:944–950 (Feb. 1994).

* cited by examiner

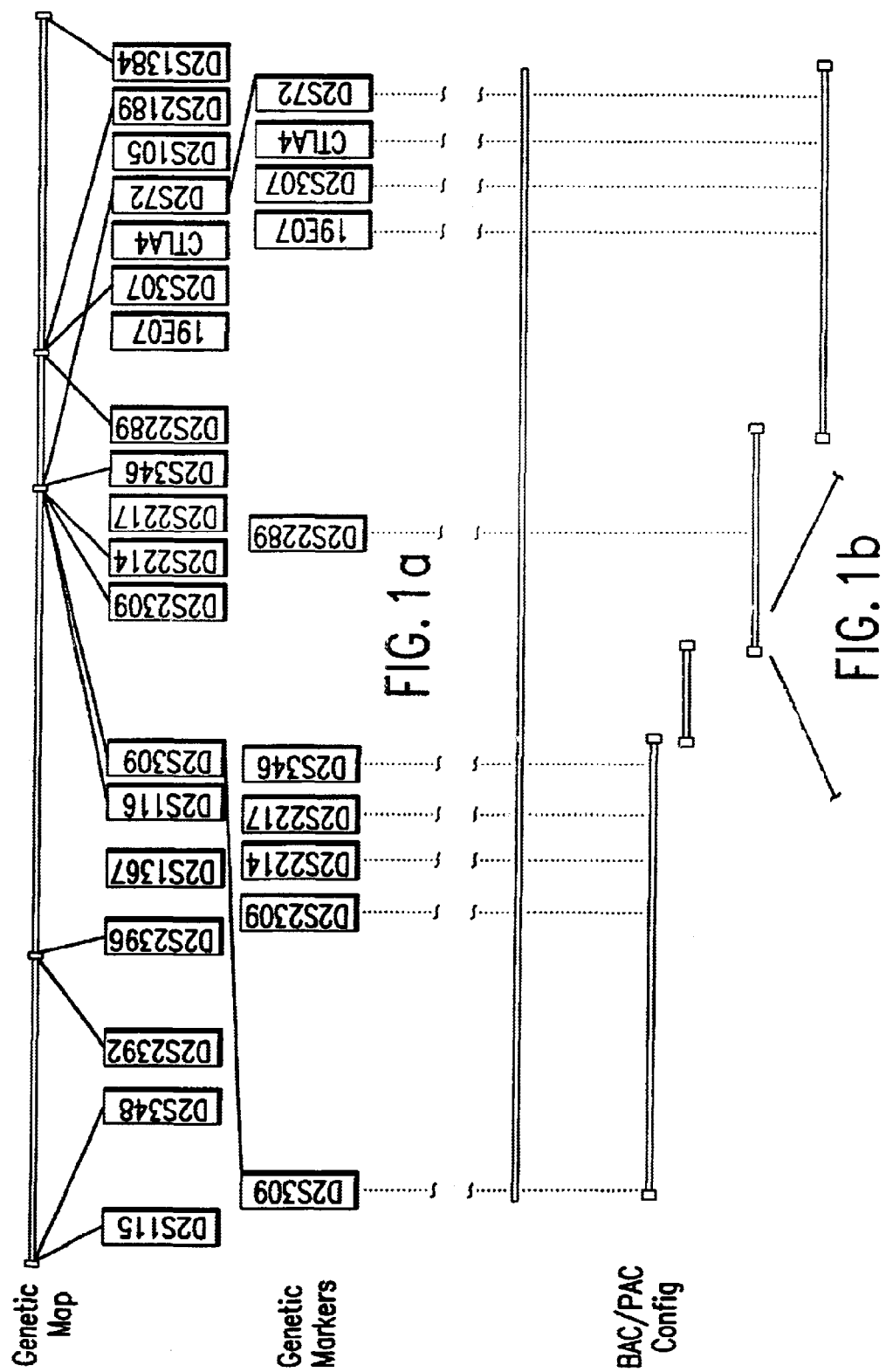

SEQUENCE LISTING

<160> NUMBER OF SEQ ID NOS: 36

<210> SEQ ID NO 1
<211> LENGTH: 3122
<212> TYPE: DNA
<213> ORGANISM: Homo Sapiens
<220> FEATURE:
<221> NAME/KEY: CDS
<222> LOCATION: (1)...(3115)

<400> SEQUENCE: 1

| atg | act | tcc | tcg | ctg | cag | cgg | ccc | tgg | cgg | gtg | ccc | tgg | cta | cca | tgg | 48 |
|---|---|---|---|---|---|---|---|---|---|---|---|---|---|---|---|---|
| Met | Thr | Ser | Ser | Leu | Gln | Arg | Pro | Trp | Arg | Val | Pro | Trp | Leu | Pro | Trp | |
| 1 | | | | 5 | | | | | 10 | | | | | 15 | | |

| acc | atc | ctg | ctg | gtc | agc | act | gcg | gct | gct | tcg | cag | aat | caa | gaa | cgg | 96 |
|---|---|---|---|---|---|---|---|---|---|---|---|---|---|---|---|---|
| Thr | Ile | Leu | Leu | Val | Ser | Thr | Ala | Ala | Ala | Ser | Gln | Asn | Gln | Glu | Arg | |
| | | | 20 | | | | | 25 | | | | | 30 | | | |

| cta | tgt | gcg | ttt | aaa | gat | ccg | tat | cag | caa | gac | ctt | ggg | ata | ggt | gag | 144 |
|---|---|---|---|---|---|---|---|---|---|---|---|---|---|---|---|---|
| Leu | Cys | Ala | Phe | Lys | Asp | Pro | Tyr | Gln | Gln | Asp | Leu | Gly | Ile | Gly | Glu | |
| | | 35 | | | | | 40 | | | | | 45 | | | | |

| agt | aga | atc | tct | cat | gaa | aat | ggg | aca | ata | tta | tgc | tcg | aaa | ggt | agc | 192 |
|---|---|---|---|---|---|---|---|---|---|---|---|---|---|---|---|---|
| Ser | Arg | Ile | Ser | His | Glu | Asn | Gly | Thr | Ile | Leu | Cys | Ser | Lys | Gly | Ser | |
| | 50 | | | | | 55 | | | | | 60 | | | | | |

| acc | tgc | tat | ggc | ctt | tgg | gag | aaa | tca | aaa | ggg | gac | ata | aat | ctt | gta | 240 |
|---|---|---|---|---|---|---|---|---|---|---|---|---|---|---|---|---|
| Thr | Cys | Tyr | Gly | Leu | Trp | Glu | Lys | Ser | Lys | Gly | Asp | Ile | Asn | Leu | Val | |
| 65 | | | | | 70 | | | | | 75 | | | | | 80 | |

| aaa | caa | gga | tgt | tgg | tct | cac | att | gga | gat | ccc | caa | gag | tgt | cac | tat | 288 |
|---|---|---|---|---|---|---|---|---|---|---|---|---|---|---|---|---|
| Lys | Gln | Gly | Cys | Trp | Ser | His | Ile | Gly | Asp | Pro | Gln | Glu | Cys | His | Tyr | |
| | | | | 85 | | | | | 90 | | | | | 95 | | |

| gaa | gaa | tgt | gta | gta | act | acc | act | cct | ccc | tca | att | cag | aat | gga | aca | 336 |
|---|---|---|---|---|---|---|---|---|---|---|---|---|---|---|---|---|
| Glu | Glu | Cys | Val | Val | Thr | Thr | Thr | Pro | Pro | Ser | Ile | Gln | Asn | Gly | Thr | |
| | | | 100 | | | | | 105 | | | | | 110 | | | |

| tac | cgt | ttc | tgc | tgt | tgt | agc | aca | gat | tta | tgt | aat | gtc | aac | ttt | act | 384 |
|---|---|---|---|---|---|---|---|---|---|---|---|---|---|---|---|---|
| Tyr | Arg | Phe | Cys | Cys | Cys | Ser | Thr | Asp | Leu | Cys | Asn | Val | Asn | Phe | Thr | |
| | | 115 | | | | | 120 | | | | | 125 | | | | |

| gag | aat | ttt | cca | cct | cct | gac | aca | aca | cca | ctc | agt | cca | cct | cat | tca | 432 |
|---|---|---|---|---|---|---|---|---|---|---|---|---|---|---|---|---|
| Glu | Asn | Phe | Pro | Pro | Pro | Asp | Thr | Thr | Pro | Leu | Ser | Pro | Pro | His | Ser | |
| | 130 | | | | | 135 | | | | | 140 | | | | | |

| ttt | aac | cga | gat | gag | aca | ata | atc | att | gct | ttg | gca | tca | gtc | tct | gta | 480 |
|---|---|---|---|---|---|---|---|---|---|---|---|---|---|---|---|---|
| Phe | Asn | Arg | Asp | Glu | Thr | Ile | Ile | Ile | Ala | Leu | Ala | Ser | Val | Ser | Val | |
| 145 | | | | | 150 | | | | | 155 | | | | | 160 | |

| tta | gct | gtt | ttg | ata | gtt | gcc | tta | tgc | ttt | gga | tac | aga | atg | ttg | aca | 528 |
|---|---|---|---|---|---|---|---|---|---|---|---|---|---|---|---|---|
| Leu | Ala | Val | Leu | Ile | Val | Ala | Leu | Cys | Phe | Gly | Tyr | Arg | Met | Leu | Thr | |
| | | | | 165 | | | | | 170 | | | | | 175 | | |

| gga | gac | cgt | aaa | caa | ggt | ctt | cac | agt | atg | aac | atg | atg | gag | gca | gca | 576 |
|---|---|---|---|---|---|---|---|---|---|---|---|---|---|---|---|---|
| Gly | Asp | Arg | Lys | Gln | Gly | Leu | His | Ser | Met | Asn | Met | Met | Glu | Ala | Ala | |
| | | | 180 | | | | | 185 | | | | | 190 | | | |

| gca | tcc | gaa | ccc | tct | ctt | gat | cta | gat | aat | ctg | aaa | ctg | ttg | gag | ctg | 624 |
|---|---|---|---|---|---|---|---|---|---|---|---|---|---|---|---|---|
| Ala | Ser | Glu | Pro | Ser | Leu | Asp | Leu | Asp | Asn | Leu | Lys | Leu | Leu | Glu | Leu | |
| | | | 195 | | | | | 200 | | | | | 205 | | | |

| att | ggc | cga | ggt | cga | tat | gga | gca | gta | tat | aaa | ggc | tcc | ttg | gat | gag | 672 |
|---|---|---|---|---|---|---|---|---|---|---|---|---|---|---|---|---|
| Ile | Gly | Arg | Gly | Arg | Tyr | Gly | Ala | Val | Tyr | Lys | Gly | Ser | Leu | Asp | Glu | |
| | | 210 | | | | | 215 | | | | | 220 | | | | |

| cgt | cca | gtt | gct | gta | aaa | gtg | ttt | tcc | ttt | gca | aac | cgt | cag | aat | ttt | 720 |
|---|---|---|---|---|---|---|---|---|---|---|---|---|---|---|---|---|
| Arg | Pro | Val | Ala | Val | Lys | Val | Phe | Ser | Phe | Ala | Asn | Arg | Gln | Asn | Phe | |
| 225 | | | | | 230 | | | | | 235 | | | | | 240 | |

| atc | aac | gaa | aag | aac | att | tac | aga | gtg | cct | ttg | atg | gaa | cat | gac | aac | 768 |
|---|---|---|---|---|---|---|---|---|---|---|---|---|---|---|---|---|
| Ile | Asn | Glu | Lys | Asn | Ile | Tyr | Arg | Val | Pro | Leu | Met | Glu | His | Asp | Asn | |
| | | | | 245 | | | | | 250 | | | | | 255 | | |

-continued

| | | |
|---|---|---|
| att gcc cgc ttt ata gtt gga gat gag aga gtc act gca gat gga cgc<br>Ile Ala Arg Phe Ile Val Gly Asp Glu Arg Val Thr Ala Asp Gly Arg<br>260                              265                    270 | 816 |
| atg gaa tat ttg ctt gtg atg gag tac tat ccc aat gga tct tta tgc<br>Met Glu Tyr Leu Leu Val Met Glu Tyr Tyr Pro Asn Gly Ser Leu Cys<br>275                          280                    285 | 864 |
| aag tat tta agt ctc cac aca agt gac tgg gta agc tct tgc cgt ctt<br>Lys Tyr Leu Ser Leu His Thr Ser Asp Trp Val Ser Ser Cys Arg Leu<br>290                          295                    300 | 912 |
| gct cat tct gtt act aga gga ctg gct tat ctt cac aca gaa tta cca<br>Ala His Ser Val Thr Arg Gly Leu Ala Tyr Leu His Thr Glu Leu Pro<br>305                          310                    315                    320 | 960 |
| cga gga gat cat tat aaa cct gca att tcc cat cga gat tta aac agc<br>Arg Gly Asp His Tyr Lys Pro Ala Ile Ser His Arg Asp Leu Asn Ser<br>                    325                    330                    335 | 1008 |
| aga aat gtc cta gtg aaa aat gat gga acc tgt gtt att agt gac ttt<br>Arg Asn Val Leu Val Lys Asn Asp Gly Thr Cys Val Ile Ser Asp Phe<br>                    340                    345                    350 | 1056 |
| gga ctg tcc atg agg ctg act gga aat aga ctg gtg cgc cca ggg gag<br>Gly Leu Ser Met Arg Leu Thr Gly Asn Arg Leu Val Arg Pro Gly Glu<br>                    355                    360                    365 | 1104 |
| gaa gat aat gca gcc ata agc gag gtt ggc act atc aga tat atg gca<br>Glu Asp Asn Ala Ala Ile Ser Glu Val Gly Thr Ile Arg Tyr Met Ala<br>370                          375                    380 | 1152 |
| cca gaa gtg cta gaa gga gct gtg aac ttg agg gac tgt gaa tca gct<br>Pro Glu Val Leu Glu Gly Ala Val Asn Leu Arg Asp Cys Glu Ser Ala<br>385                          390                    395                    400 | 1200 |
| ttg aaa caa gta gac atg tat gct ctt gga cta atc tat tgg gag ata<br>Leu Lys Gln Val Asp Met Tyr Ala Leu Gly Leu Ile Tyr Trp Glu Ile<br>                    405                    410                    415 | 1248 |
| ttt atg aga tgt aca gac ctc ttc cca ggg gaa tcc gta cca gag tac<br>Phe Met Arg Cys Thr Asp Leu Phe Pro Gly Glu Ser Val Pro Glu Tyr<br>                    420                    425                    430 | 1296 |
| cag atg gct ttt cag aca gag gtt gga aac cat ccc act ttt gag gat<br>Gln Met Ala Phe Gln Thr Glu Val Gly Asn His Pro Thr Phe Glu Asp<br>                    435                    440                    445 | 1344 |
| atg cag gtt ctc gtg tct agg gaa aaa cag aga ccc aag ttc cca gaa<br>Met Gln Val Leu Val Ser Arg Glu Lys Gln Arg Pro Lys Phe Pro Glu<br>450                          455                    460 | 1392 |
| gcc tgg aaa gaa aat agc ctg gca gtg agg tca ctc aag gag aca atc<br>Ala Trp Lys Glu Asn Ser Leu Ala Val Arg Ser Leu Lys Glu Thr Ile<br>465                          470                    475                    480 | 1440 |
| gaa gac tgt tgg gac cag gat gca gag gct cgg ctt act gca cag tgt<br>Glu Asp Cys Trp Asp Gln Asp Ala Glu Ala Arg Leu Thr Ala Gln Cys<br>                    485                    490                    495 | 1488 |
| gct gag gaa agg atg gct gaa ctt atg atg att tgg gaa aga aac aaa<br>Ala Glu Glu Arg Met Ala Glu Leu Met Met Ile Trp Glu Arg Asn Lys<br>500                          505                    510 | 1536 |
| tct gtg agc cca aca gtc aat cca atg tct act gct atg cag aat gaa<br>Ser Val Ser Pro Thr Val Asn Pro Met Ser Thr Ala Met Gln Asn Glu<br>                    515                    520                    525 | 1584 |
| cgc aac ctg tca cat aat agg cgt gtg cca aaa att ggt cct tat cca<br>Arg Asn Leu Ser His Asn Arg Arg Val Pro Lys Ile Gly Pro Tyr Pro<br>530                          535                    540 | 1632 |
| gat tat tct tcc tcc tca tac att gaa gac tct atc cat cat act gac<br>Asp Tyr Ser Ser Ser Ser Tyr Ile Glu Asp Ser Ile His His Thr Asp<br>545                          550                    555                    560 | 1680 |
| agc atc gtg aag aat att tcc tct gag cat tct atg tcc agc aca cct<br>Ser Ile Val Lys Asn Ile Ser Ser Glu His Ser Met Ser Ser Thr Pro<br>                    565                    570                    575 | 1728 |

```
ttg act ata ggg gaa aaa aac cga aat tca att aac tat gaa cga cag      1776
Leu Thr Ile Gly Glu Lys Asn Arg Asn Ser Ile Asn Tyr Glu Arg Gln
            580                 585                 590 caa gca caa gct cga atc ccc agc cct gaa aca agt gtc acc agc ctc      1824
Gln Ala Gln Ala Arg Ile Pro Ser Pro Glu Thr Ser Val Thr Ser Leu
        595                 600                 605 tcc acc aac aca aca acc aca aac acc aca gga ctc acg cca agt act      1872
Ser Thr Asn Thr Thr Thr Thr Asn Thr Thr Gly Leu Thr Pro Ser Thr
        610                 615                 620 ggc atg act act ata tct gag atg cca tac cca gat gaa aca aat ctg      1920
Gly Met Thr Thr Ile Ser Glu Met Pro Tyr Pro Asp Glu Thr Asn Leu
625                 630                 635                 640 cat acc aca aat gtt gca cag tca att ggg cca acc cct gtc tgc tta      1968
His Thr Thr Asn Val Ala Gln Ser Ile Gly Pro Thr Pro Val Cys Leu
            645                 650                 655 cag ctg aca gaa gaa gac ttg gaa acc aac aag cta gac cca aaa gaa      2016
Gln Leu Thr Glu Glu Asp Leu Glu Thr Asn Lys Leu Asp Pro Lys Glu
        660                 665                 670 gtt gat aag aac ctc aag gaa agc tct gat gag aat ctc atg gag cac      2064
Val Asp Lys Asn Leu Lys Glu Ser Ser Asp Glu Asn Leu Met Glu His
        675                 680                 685 tct ctt aaa cag ttc agt ggc cca gac cca ctg agc agt act agt tct      2112
Ser Leu Lys Gln Phe Ser Gly Pro Asp Pro Leu Ser Ser Thr Ser Ser
            690                 695                 700 agc ttg ctt tac cca ctc ata aaa ctt gca gta gaa gca act gga cag      2160
Ser Leu Leu Tyr Pro Leu Ile Lys Leu Ala Val Glu Ala Thr Gly Gln
705                 710                 715                 720 cag gac ttc aca cag act gca aat ggc caa gca tgt ttg att cct gat      2208
Gln Asp Phe Thr Gln Thr Ala Asn Gly Gln Ala Cys Leu Ile Pro Asp
            725                 730                 735 gtt ctg cct act cag atc tat cct ctc ccc aag cag cag aac ctt ccc      2256
Val Leu Pro Thr Gln Ile Tyr Pro Leu Pro Lys Gln Gln Asn Leu Pro
        740                 745                 750 aag aga cct act agt ttg cct ttg aac acc aaa aat tca aca aaa gag      2304
Lys Arg Pro Thr Ser Leu Pro Leu Asn Thr Lys Asn Ser Thr Lys Glu
        755                 760                 765 ccc cgg cta aaa ttt ggc agc aag cac aaa tca aac ttg aaa caa gtc      2352
Pro Arg Leu Lys Phe Gly Ser Lys His Lys Ser Asn Leu Lys Gln Val
770                 775                 780 gaa act gga gtt gcc aag atg aat aca atc aat gca gca gaa cct cat      2400
Glu Thr Gly Val Ala Lys Met Asn Thr Ile Asn Ala Ala Glu Pro His
            785                 790                 795                 800 gtg gtg aca gtc acc atg aat ggt gtg gca ggt aga aac cac agt gtt      2448
Val Val Thr Val Thr Met Asn Gly Val Ala Gly Arg Asn His Ser Val
                    805                 810                 815 aac tcc cat gct gcc aca acc caa tat gcc aat agg aca gta cta tct      2496
Asn Ser His Ala Ala Thr Thr Gln Tyr Ala Asn Arg Thr Val Leu Ser
        820                 825                 830 ggc caa aca acc aac ata gtg aca cat agg gcc caa gaa atg ttg cag      2544
Gly Gln Thr Thr Asn Ile Val Thr His Arg Ala Gln Glu Met Leu Gln
        835                 840                 845 aat cag ttt att ggt gag gac acc cgg ctg aat att aat tcc agt cct      2592
Asn Gln Phe Ile Gly Glu Asp Thr Arg Leu Asn Ile Asn Ser Ser Pro
850                 855                 860 gat gag cat gag cct tta ctg aga cga gag caa caa gct ggc cat gat      2640
Asp Glu His Glu Pro Leu Leu Arg Arg Glu Gln Gln Ala Gly His Asp
865                 870                 875                 880 gaa ggt gtt ctg gat cgt ctt gtg gac agg agg gaa cgg cca cta gaa      2688
Glu Gly Val Leu Asp Arg Leu Val Asp Arg Arg Glu Arg Pro Leu Glu
```

-continued

| | | | 885 | | | | | 890 | | | | | 895 | | | |
|---|---|---|---|---|---|---|---|---|---|---|---|---|---|---|---|---|
| ggt | ggc | cga | act | aat | tcc | aat | aac | aac | agc | aat | cca | tgt | tca | gaa | | 2736 |
| Gly | Gly | Arg | Thr | Asn | Ser | Asn | Asn | Asn | Ser | Asn | Pro | Cys | Ser | Glu | | |
| | | | 900 | | | | | 905 | | | | | 910 | | | |

```
caa gat gtt ctt gca cag ggt gtt cca agc aca gca gca gat cct ggg        2784
Gln Asp Val Leu Ala Gln Gly Val Pro Ser Thr Ala Ala Asp Pro Gly
        915                 920                 925 cca tca aag ccc aga aga gca cag agg cct aat tct ctg gat ctt tca        2832
Pro Ser Lys Pro Arg Arg Ala Gln Arg Pro Asn Ser Leu Asp Leu Ser
930                 935                 940 gcc aca aat gtc ctg gat ggc agc agt ata cag ata ggt gag tca aca        2880
Ala Thr Asn Val Leu Asp Gly Ser Ser Ile Gln Ile Gly Glu Ser Thr
945                 950                 955                 960 caa gat ggc aaa tca gga tca ggt gaa aag atc aag aaa cgt gtg aaa        2928
Gln Asp Gly Lys Ser Gly Ser Gly Glu Lys Ile Lys Lys Arg Val Lys
        965                 970                 975 act ccc tat tct ctt aag cgg tgg cgc ccc tcc acc tgg gtc atc tcc        2976
Thr Pro Tyr Ser Leu Lys Arg Trp Arg Pro Ser Thr Trp Val Ile Ser
        980                 985                 990 act gaa tcg ctg gac tgt gaa gtc aac aat aat ggc agt aac agg gca        3024
Thr Glu Ser Leu Asp Cys Glu Val Asn Asn Asn Gly Ser Asn Arg Ala
        995                 1000                1005 gtt cat tcc aaa tcc agc act gct gtt tac ctt gca gaa gga ggc act        3072
Val His Ser Lys Ser Ser Thr Ala Val Tyr Leu Ala Glu Gly Gly Thr
        1010                1015                1020 gct aca acc atg gtg tct aaa gat ata gga atg aac tgt ctg t              3115
Ala Thr Thr Met Val Ser Lys Asp Ile Gly Met Asn Cys Leu
1025                1030                1035 gaaatgt                                                                 3122
```

<210> SEQ ID NO 2
<211> LENGTH: 1038
<212> TYPE: PRT
<213> ORGANISM: Homo Sapiens

<400> SEQUENCE: 2

```
Met Thr Ser Ser Leu Gln Arg Pro Trp Arg Val Pro Trp Leu Pro Trp
 1               5                  10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
```

-continued

```
                165                 170                 175
Gly Asp Arg Lys Gln Gly Leu His Ser Met Asn Met Met Glu Ala Ala
                180                 185                 190
Ala Ser Glu Pro Ser Leu Asp Leu Asp Asn Leu Lys Leu Leu Glu Leu
                195                 200                 205
Ile Gly Arg Gly Arg Tyr Gly Ala Val Tyr Lys Gly Ser Leu Asp Glu
                210                 215                 220
Arg Pro Val Ala Val Lys Val Phe Ser Phe Ala Asn Arg Gln Asn Phe
225                 230                 235                 240
Ile Asn Glu Lys Asn Ile Tyr Arg Val Pro Leu Met Glu His Asp Asn
                245                 250                 255
Ile Ala Arg Phe Ile Val Gly Asp Glu Arg Val Thr Ala Asp Gly Arg
                260                 265                 270
Met Glu Tyr Leu Leu Val Met Glu Tyr Tyr Pro Asn Gly Ser Leu Cys
                275                 280                 285
Lys Tyr Leu Ser Leu His Thr Ser Asp Trp Val Ser Ser Cys Arg Leu
                290                 295                 300
Ala His Ser Val Thr Arg Gly Leu Ala Tyr Leu His Thr Glu Leu Pro
305                 310                 315                 320
Arg Gly Asp His Tyr Lys Pro Ala Ile Ser His Arg Asp Leu Asn Ser
                325                 330                 335
Arg Asn Val Leu Val Lys Asn Asp Gly Thr Cys Val Ile Ser Asp Phe
                340                 345                 350
Gly Leu Ser Met Arg Leu Thr Gly Asn Arg Leu Val Arg Pro Gly Glu
                355                 360                 365
Glu Asp Asn Ala Ala Ile Ser Glu Val Gly Thr Ile Arg Tyr Met Ala
                370                 375                 380
Pro Glu Val Leu Glu Gly Ala Val Asn Leu Arg Asp Cys Glu Ser Ala
385                 390                 395                 400
Leu Lys Gln Val Asp Met Tyr Ala Leu Gly Leu Ile Tyr Trp Glu Ile
                405                 410                 415
Phe Met Arg Cys Thr Asp Leu Phe Pro Gly Glu Ser Val Pro Glu Tyr
                420                 425                 430
Gln Met Ala Phe Gln Thr Glu Val Gly Asn His Pro Thr Phe Glu Asp
                435                 440                 445
Met Gln Val Leu Val Ser Arg Glu Lys Gln Arg Pro Lys Phe Pro Glu
450                 455                 460
Ala Trp Lys Glu Asn Ser Leu Ala Val Arg Ser Leu Lys Glu Thr Ile
465                 470                 475                 480
Glu Asp Cys Trp Asp Gln Asp Ala Glu Ala Arg Leu Thr Ala Gln Cys
                485                 490                 495
Ala Glu Glu Arg Met Ala Glu Leu Met Met Ile Trp Glu Arg Asn Lys
                500                 505                 510
Ser Val Ser Pro Thr Val Asn Pro Met Ser Thr Ala Met Gln Asn Glu
                515                 520                 525
Arg Asn Leu Ser His Asn Arg Arg Val Pro Lys Ile Gly Pro Tyr Pro
                530                 535                 540
Asp Tyr Ser Ser Ser Ser Tyr Ile Glu Asp Ser Ile His His Thr Asp
545                 550                 555                 560
Ser Ile Val Lys Asn Ile Ser Ser Glu His Ser Met Ser Ser Thr Pro
                565                 570                 575
Leu Thr Ile Gly Glu Lys Asn Arg Asn Ser Ile Asn Tyr Glu Arg Gln
                580                 585                 590
```

```
Gln Ala Gln Ala Arg Ile Pro Ser Pro Glu Thr Ser Val Thr Ser Leu
            595                 600                 605

Ser Thr Asn Thr Thr Thr Thr Asn Thr Thr Gly Leu Thr Pro Ser Thr
    610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
            660                 665                 670

Val Asp Lys Asn Leu Lys Glu Ser Ser Asp Glu Asn Leu Met Glu His
            675                 680                 685

Ser Leu Lys Gln Phe Ser Gly Pro Asp Pro Leu Ser Ser Thr Ser Ser
    690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
            740                 745                 750

Lys Arg Pro Thr Ser Leu Pro Leu Asn Thr Lys Asn Ser Thr Lys Glu
            755                 760                 765

Pro Arg Leu Lys Phe Gly Ser Lys His Lys Ser Asn Leu Lys Gln Val
    770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Arg Thr Val Leu Ser
            820                 825                 830

Gly Gln Thr Thr Asn Ile Val Thr His Arg Ala Gln Glu Met Leu Gln
            835                 840                 845

Asn Gln Phe Ile Gly Glu Asp Thr Arg Leu Asn Ile Asn Ser Ser Pro
    850                 855                 860

Asp Glu His Glu Pro Leu Leu Arg Arg Glu Gln Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Ser Asn Pro Cys Ser Glu
            900                 905                 910

Gln Asp Val Leu Ala Gln Gly Val Pro Ser Thr Ala Ala Asp Pro Gly
            915                 920                 925

Pro Ser Lys Pro Arg Arg Ala Gln Arg Pro Asn Ser Leu Asp Leu Ser
    930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val Asn Asn Asn Gly Ser Asn Arg Ala
            995                 1000                1005
```

Val His Ser Lys Ser Ser Thr Ala Val Tyr Leu Ala Glu Gly Gly Thr
     1010                1015                1020

Ala Thr Thr Met Val Ser Lys Asp Ile Gly Met Asn Cys Leu
1025                1030                1035

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 3
agctaggtcc tctcatcagc                                            20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 4
cagccgcagt gctgaccagc                                            20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 5
gtcattcgga taagacaaag                                            20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 6
tttaacatac tcccatgtcc                                            20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 7
tagcttacac gtactctcac                                            20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 8
cctggcttca accttgaatg                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 9
gggtacagcc tttctaaagg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 10
gatactattg aggctgggtg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 11
gctgctaatc tttctgcagc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 12
gaatgaagtc actgttccag                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 13
cagagagctg tagcattctg                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

```
<400> SEQUENCE: 14
aagtgatcca cctgccttag                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 15
actcttcatg ttaaagtgag                                                    20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 16
ctttgaagat ataattaaaa tttcc                                              25

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 17
cacctggcca gtagatgttt                                                    20

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 18
tgttcaatag tccctttat tcattg                                              26

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 19
ctaatttgca tcctgctgct                                                    20

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 20
```
tgttcttcag aatatgctac gttctc                                              26

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 21
ttgtggcatt aggcaactcc                                                     20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 22
gcctgaaggg gatgaaaaa                                                      19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 23
ccacacccct tagggtctta                                                     20

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 24
cacatggttt gacatgtact ttg                                                 23

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 25
catcagagct ttccttgagg tt                                                  22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 26

```
cagaggtgtt aaatttggag                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 27
tctacctgcc acaccattca                                              20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 28
tggaaaccaa caagctagac c                                            21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 29
ccccaaaaga cacacaggag                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 30
tgaatggtgt ggcaggtaga                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 31
gctgacagga ggataaagca                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence; Note =
      Syntheic Construct

<400> SEQUENCE: 32
caccctcctg agacattggt                                              20
```

-continued

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence; Note = Syntheic Construct

<400> SEQUENCE: 33
acccaatatg ccaatgggac                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence; Note = Syntheic Construct

<400> SEQUENCE: 34
ttcgccacct tctagtggct                                              20

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence; Note = Syntheic Construct

<400> SEQUENCE: 35
catgtggtaa actgaaaagc tca                                          23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence; Note = Syntheic Construct

<400> SEQUENCE: 36
ttgagaccac tttgatacac aca                                          23

METHOD OF DIAGNOSING PULMONARY HYPERTENSION

CROSS-REFERENCE TO RELATED APPLICATIONS

This application claims benefit of U.S. Provisional Application No. 60/218,740, filed Jul. 17, 2000, and U.S. Provisional Application No. 60/220,133, filed Jul. 21, 2000. Application Ser. No. 60/218,740, filed Jul. 17, 2000, and U.S. Provisional Application No. 60/220,133, filed Jul. 21, 2000, are hereby incorporated herein by reference.

STATEMENT REGARDING FEDERALLY SPONSORED RESEARCH

Some of the research on which the present disclosure is based was funded by National Institutes of Health Grants HL 48164 and HL 61997.

FIELD OF THE INVENTION

This invention relates generally to a method of identifying an individual having an increased susceptibility to developing Familial Primary Pulmonary Hypertension (FPPH), as well as to a method for diagnosing an individual suffering from FPPH. The invention also relates to a method of identifying an individual having an increased susceptibility to developing non-familial, or sporadic, Primary Pulmonary Hypertension (PPH), as well as to a method for diagnosing an individual suffering from sporadic PPH. The invention also relates to a method of identifying an agent capable of altering the symptoms of PPH in an individual suffering from familial or sporadic PPH, comprising contacting a test agent with Bone Morphogenic Protein Receptor II (BMPR-II) and determining whether the test agent alters BMPR-II activity, wherein an alteration in BMPR-II activity in the presence of the test agent as compared with BMPR-II activity in the absence of the test agent indicates that the test agent is capable of altering the symptoms of PPH in an individual suffering from familial or sporadic PPH.

BACKGROUND OF THE INVENTION

Primary pulmonary hypertension (PH) is characterized by sustained elevation of pulmonary artery pressure (greater than 25 mmHg at rest and greater than 30 mmHg during exercise) and with no identifiable cause, such as recurrent thromboembolism, chronic hypoxic lung disease or left-sided cardiac disease. PPH is twice as common in females than males and symptoms develop typically in the $3^{rd}$ and $4^{th}$ decades of life, although the disease may occur at any age. Despite advances in therapy, mortality in PPH remains high with mean survival from onset of disease only 2.5 year.

At least 6% of individuals diagnosed with PPH have a known family history of the disorder. The disease can be classified as being either familial (more than one affected relative has been identified in at least 6% of cases (familial PPH; MIM 178600) (ref. 3)) or sporadic. Familial PPH (FPPH) segregates as an autosomal dominant disorder, with markedly reduced penetrance.

There is a need to identify the genetic basis for this devastating disease in order to better diagnose and treat patients suffering from PPH.

BRIEF SUMMARY OF THE INVENTION

The invention relates to a method of identifying a subject having an increased susceptibility for developing pulmonary hypertension, comprising detecting a mutant Bone Morphogenic Protein Receptor II (BMPR-II) polypeptide or a mutated Bone Morphogenic Protein Receptor 2 (BMPR2) nucleic acid in the subject, thereby identifying a subject having an increased susceptibility for developing pulmonary hypertension. Wild-type BMPR2 nucleotide sequence is SEQ ID NO:1. Wild-type BMPR-II amino acid sequence is SEQ ID NO:2.

In one aspect, the mutated BMPR2 nucleic acid or mutant BMPR-II polypeptide has a sequence associated with pulmonary hypertension.

In another aspect, the mutated BMPR2 nucleic acid comprises a missense mutation.

In yet another aspect, the mutated BMPR2 nucleic acid comprises a nonsense mutation.

In another aspect, the mutated BMPR2 nucleic acid comprises a deletion mutation.

In another aspect, the mutated BMPR2 nucleic acid comprises an insertion mutation.

In another aspect, the mutated BMPR2 nucleic acid comprises a truncation mutation. Preferably, the mutated BMPR2 nucleic acid is truncated at a nucleotide position of the sequence set forth in SEQ ID NO:1 which is 3' to nucleotide position 2695.

In another aspect, the subject having an increased susceptibility for developing pulmonary hypertension is identified by detecting a BMPR2 nucleic acid having a sequence associated with pulmonary hypertension.

In a preferred aspect, the pulmonary hypertension is primary pulmonary hypertension. In another aspect, the pulmonary hypertension is secondary pulmonary hypertension.

In various preferred embodiments, the mutated BMPR2 nucleic acid can include a missense mutation or a nonsense mutation.

In another aspect, the invention features a method of identifying a mutant BMPR-II polypeptide or a mutated BMPR2 nucleic acid, including detecting, in a patient with PPH, a BMPR-II polypeptide that is not present in normal subjects or a BMPR2 nucleic acid that is not present in normal subjects, thereby identifying a mutant BMPR-II polypeptide or a mutated BMPR2 nucleic acid.

In another aspect, the invention features a method of increasing BMPR-II biological activity.

In another aspect, the invention features a method of decreasing BMPR-II biological activity.

In another aspect, the invention features a method of identifying a compound that modulates the biological activity of a BMPR-II polypeptide, including: a) contacting a sample including a BMPR-II polypeptide or a BMPR2 nucleic acid with the compound; and b) measuring BMPR-II biological activity in the sample, whereby an increase or decrease in BMPR-II biological activity, compared to BMPR-II biological activity in an identical sample not contacted with the compound, identifies a compound that modulates the biological activity of the BMPR-II polypeptide.

In various embodiments of this aspect of the invention, BMPR-II biological activity is increased or decreased; the BMPR-II polypeptide is a wild-type BMPR-II polypeptide or the BMPR2 nucleic acid is a wild-type BMPR2 nucleic acid; the BMPR-II polypeptide is a polymorphic variant of a BMPR-II polypeptide or the BMPR2 nucleic acid is a polymorphic variant of a BMPR2 nucleic acid; or the BMPR-II polypeptide is a mutant BMPR-II polypeptide or the BMPR2 nucleic acid is a mutated BMPR2 nucleic acid.

In another aspect, the invention features a non-human mammal having a deleted, mutated, or polymorphic variant BMPR2 gene. In various aspects of the twelfth aspect of the invention, the non-human mammal is a mouse; and/or the non-human mammal is homozygous for the deleted, mutated, or polymorphic variant BMPR2 gene.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWING

FIGS. 1A–1C are diagrams showing the physical map of the PPH1 interval at 2q33. FIG. 1A shows the position of microsatellite markers. The markers are, from left to right, D2S115, D2S348, D2S2392, D2S2396, D2S1367, D2S116, D2S309, D2S2309, D2S2214, D2S2217, D2S346, D2S2289, 19E07, D2S307, CTLA4, D2S72, D2S105, D2S2189, D2S1384. FIG. 1B shows the physical map contig (BAC/PAC) of the region surrounding BMPR2 including other genes analysed in the examples (12). FIG. 1C shows the BMPR2 genomic structure, determined by analysis of available sequence data for BAC clone RP11-345N12 as well as sequence analysis of additional BAC clones identified by library screening as shown (not to scale).

DETAILED DESCRIPTION OF THE INVENTION

Figure 1C:
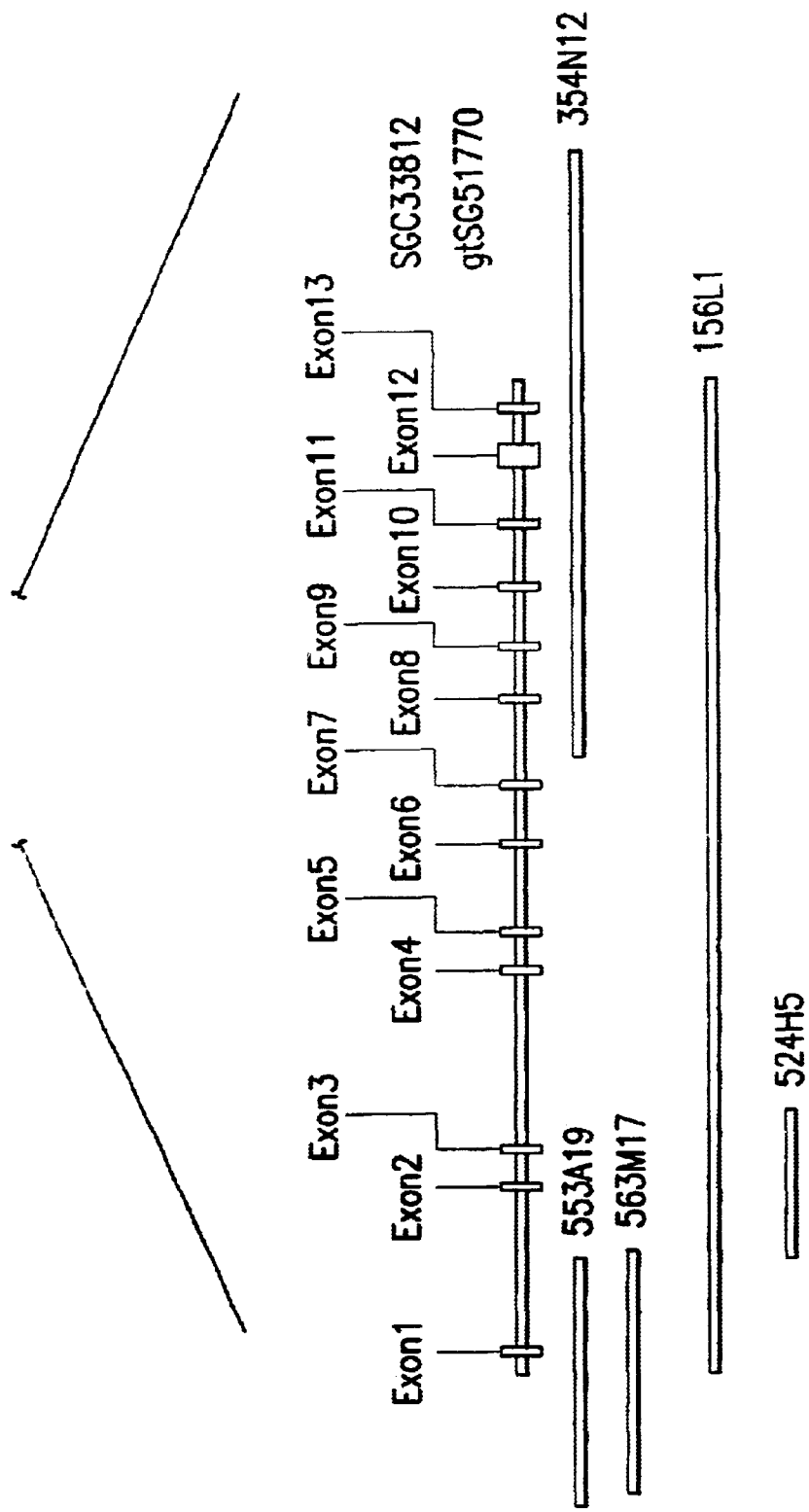
Figure 2:
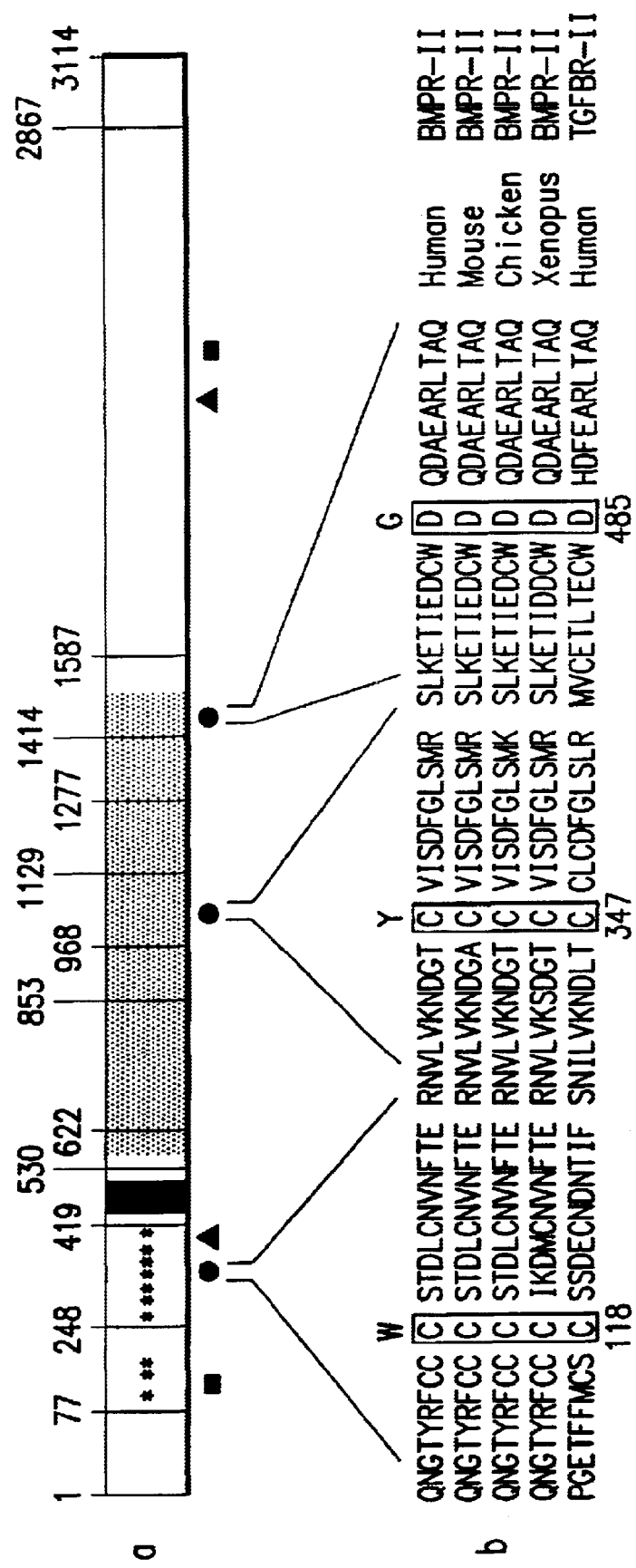
FIG. 2A is a diagram of the structure of BMPR2 cDNA. The location of the exons are indicated by the nucleotide start position in the cDNA. The cysteine residues within the extracellular domain are each denoted by *. The filled in box represents the transmembrane domain and the stippled area identifies the region encoding the receptor kinase domain.
FIG. 2B is a diagram of BLAST homology results showing protein similarity of human BMPR-II with receptors in other species and human TGF-β receptor type II (TGFBR-II). Amino acid positions are shown together with the codon substitutions of conserved amino acids (boxed).
Figure 3:
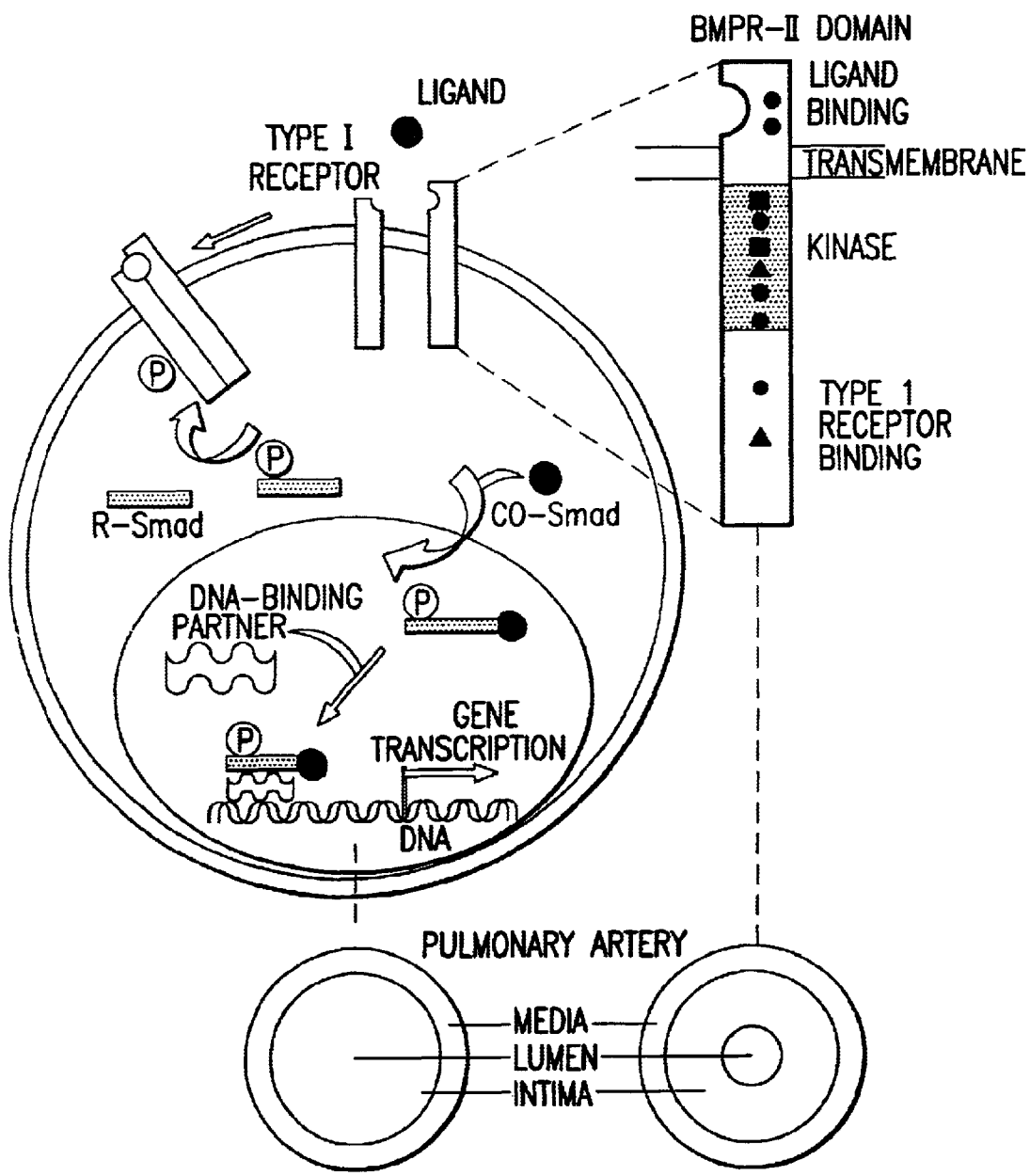
FIG. 3 is a diagram of a basic function of BMPR-II. Two BMP type I receptors (BMPRIA and BMPRIB) and a single BMP type II receptor have been identified in mammals as serine/threonine kinase receptors. Following ligand binding to BMPR-II, this receptor forms a heteromeric complex with a type I receptor, resulting in activation of the type I receptor kinase domain which intiates phosphorylation of cytoplasmic signalling proteins, termed Smads, responsible for signal transduction.

The invention relates to the surprising discovery that FPPH is caused by mutations in the gene encoding a TGF-β type II receptor, BMPR-II. The invention provides a method of identifying a subject having an increased susceptibility for developing pulmonary hypertension, comprising detecting a mutant Bone Morphogenic Protein Receptor II (BMPR-II) polypeptide or a mutated BMPR2 nucleic acid in the subject, thereby identifying a subject having an increased susceptibility for developing pulmonary hypertension. BMPR2 refers to the gene (or other nucleic acid) encoding a BMPR-II polypeptide. BMPR-II refers to the polypeptide encoded by a BMPR2 gene. Both of these terms are used herein as general identifiers. Thus, for example, a BMPR2 gene or nucleic acid refers to any gene or nucleic acid identified with or derived from a wild-type BMPR2 gene. For example, a mutant BMPR2 gene is a form of BMPR2 gene.

In a preferred embodiment, the pulmonary hypertension is primary pulmonary hypertension. In another embodiment, the pulmonary hypertension is secondary pulmonary hypertension.

As used in the specification and the appended claims, the singular forms "a," "an" and "the" include plural referents unless the context clearly dictates otherwise. Thus, for example, "a molecule" can mean a single molecule or more than one molecule.

By "about" is meant ±10% of a recited value.

By "BMPR-II biological activity" is meant any physiological function attributable to a BMPR-II polypeptide molecule, including signal transduction. BMPR-II biological activity, as referred to herein, is relative to that of the normal BMPR-II polypeptide molecule. It may be desirable to increase or decrease BMPR-II biological activity.

Mechanisms by which a compound may increase BMPR-II biological activity include, but are not limited to, mimicry of endogenous BMPR-II polypeptide activity; stimulation of the activity of a less active or inactive version (for example, a mutant) of the BMPR-II polypeptide; or increasing the amount of BMPR-II polypeptide in a cell (for example, by stimulating BMPR2 transcription and/or translation or by inhibiting BMPR2 mRNA or polypeptide degradation).

BMPR-II biological activity in a sample, such as a cell, tissue, or animal, may be indirectly measured by measuring the relative amount of BMPR2 mRNA (for example, by reverse transcription-polymerase chain reaction (RT-PCR) amplification, ribonuclease protection assay or Northern hybridization); the level of BMPR-II polypeptide (for example, by ELISA or Western blotting); or the activity of a reporter gene under the transcriptional regulation of a BMPR2 transcriptional regulatory region (by reporter gene assay, for example, employing beta-galactosidase, chloramphenicol acetyltransferase (CAT), luciferase, or green fluorescent protein, as is well known in the art). For example, a compound that increases the amount of wild-type BMPR-II polypeptide (or any other version of the polypeptide that maintains at least some activity) in a cell is a compound that increases biological activity of BMPR-II.

By "BMPR-II polypeptide" is meant a polypeptide that has, or is related to, the amino acid sequence of SEQ ID NO:2. A BMPR-II polypeptide contains an amino acid sequence that bears at least 80% sequence identity, preferably at least 85% sequence identity, more preferably at least 90% sequence identity, and most preferably at least 95%, 96%, 97%, 98%, 99%, or 100% sequence identity to the amino acid sequence of SEQ ID NO:2.

By "wild-type BMPR-II polypeptide" is meant a BMPR-I polypeptide that has the amino acid sequence of SEQ ID NO:2.

By "wild-type BMPR2 nucleic acid" is meant a nucleic acid that encodes a wild-type BMPR-II polypeptide. An example of a wild-type BMPR2 nucleic acid is SEQ ID NO:1. Other wild-type BMPR2 nucleic acids include those containing introns, such as genomic BMPR2 nucleic acid.

By "polymorphic variant of a BMPR-II polypeptide" is meant a BMPR-II polypeptide containing an amino acid change, relative to wild-type, that does not result in an increase susceptibility to PPH. Such polymorphic amino acid variations in BMPR-II are seen in both PPH patients and in normal individuals.

By "mutant BMPR-II polypeptide" is meant a BMPR-II polypeptide having an amino acid sequence that differs from the sequence of a wild-type BMPR-II polypeptide. One example of a wild-type BMPR-II polypeptide is a polypeptide having the amino acid sequence set forth in SEQ ID NO:2.

By "mutated BMPR2 nucleic acid" is meant a nucleic acid having a nucleotide sequence that differs from the sequence of the wild-type BMPR2 nucleic acid. One example of a wild-type BMPR2 nucleic acid is a nucleic acid having the nucleotide sequence set forth in SEQ ID NO:1. A "mutated nucleic acid" is also a nucleic acid that encodes a BMPR-II polypeptide having an amino acid sequence that differs from the sequence of a wild-type BMPR2 polypeptide. One example of a wild-type BMPR-II polypeptide is a polypeptide having the amino acid sequence set forth in SEQ ID NO:2. A mutated nucleic acid also includes a nucleic acid having a mutation (relative to the wild-type nucleic acid) in noncoding sequences, such as 5' or 3' sequences or intronic sequences.

By "increased susceptibility for developing pulmonary hypertension" is meant a subject who has a greater than normal chance of developing pulmonary hypertension, compared to the general population. Such subjects include, for example, a subject that harbors a mutation in a BMPR2 gene such that biological activity of BMPR-II is altered.

By "test compound" is meant a molecule, be it naturally occurring or artificially derived, that is surveyed for its ability to modulate BMPR-II activity. Test compounds may include, for example, peptides, polypeptides, synthesized organic molecules, naturally occurring organic molecules, nucleic acid molecules, and components thereof.

By "sample" is meant an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

By "modulate" is meant to alter, by increase or decrease.

By "normal subject" is meant an individual who does not have an increased susceptibility for developing pulmonary hypertension.

By an "effective amount" of a compound as provided herein is meant a sufficient amount of the compound to provide the desired effect. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

By "isolated polypeptide" or "purified polypeptide" is meant a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length polypeptides.

By "isolated nucleic acid" or "purified nucleic acid" is meant DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

By a "transgene" is meant a nucleic acid sequence that is inserted by artifice into a cell and becomes a part of the genome of that cell and its progeny. Such a transgene may be (but is not necessarily) partly or entirely heterologous (for example, derived from a different species) to the cell.

By "transgenic animal" an animal comprising a transgene as described above. Transgenic animals are made by techniques that are well known in the art.

By "knockout mutation" is meant an alteration in the nucleic acid sequence that reduces the biological activity of the polypeptide normally encoded therefrom by at least 80% relative to the unmutated gene. The mutation may, without limitation, be an insertion, deletion, frameshift, or missense mutation. A "knockout animal," for example, a knockout mouse, is an animal containing a knockout mutation. The knockout animal may be heterozygous or homozygous for the knockout mutation. Such knockout animals are generated by techniques that are well known in the art. A preferred form of knockout mutation is one where the biological activity of the BMPR-II polypeptide is not completely eliminated.

By "treat" is meant to administer a compound or molecule of the invention to a subject, such as a human or other mammal (for example, an animal model), that has an increased susceptibility for developing pulmonary hypertension, or that has pulmonary hypertension, in order to prevent or delay a worsening of the effects of the disease or condition, or to partially or fully reverse the effects of the disease.

By "prevent" is meant to minimize the chance that a subject who has an increased susceptibility for developing pulmonary hypertension will develop pulmonary hypertension.

By "specifically binds" is meant that an antibody recognizes and physically interacts with its cognate antigen (for example, a BMPR-II polypeptide) and does not significantly recognize and interact with other antigens; such an antibody may be a polyclonal antibody or a monoclonal antibody, which are generated by techniques that are well known in the art.

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for BMPR2 nucleic acids (for example, genes and/or mRNAs) have at least 80%–90% sequence complementarity, preferably at least 91%–95% sequence complementarity, more preferably at least 96%–99% sequence complementarity, and most preferably 100% sequence complementarity to the region of the BMPR2 nucleic acid to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "specifically hybridizes" is meant that a probe, primer, or oligonucleotide recognizes and physically interacts (that is, base-pairs) with a substantially complementary nucleic acid (for example, a BMPR2 nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M NaHPO$_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. See, for example, F. Ausubel et al., *Current Protocols in Molecular Biology*, John Wiley & Sons, New York, N.Y., 1998.

By "familial mutation" or "inherited mutation" is meant a mutation in an individual that was inherited from a parent and that was present in somatic cells of the parent. By "sporadic mutation" or "spontaneous mutation" is meant a mutation in an individual that arose in the individual and was not present in a parent of the individual.

By "BMPR2 RNA function" is meant a function of the RNA other than the state of coding for an amino acid sequence. For example, BMPR2 RNA production, stability, processing (including splicing), transport, and the ability to be translated are BMPR2 RNA functions. By "altered BMPR2 RNA function" is meant an alteration of BMPR2 RNA function relative to the function of wild-type BMPR2 RNA.

As set forth herein, nucleotides are numbered according to the cDNA sequence for BMPR2 (SEQ ID NO:1), with the adenosine of the initiation codon assigned position 1.

(Kawabata, M., Chytil, A. & Moses, H. L. Cloning of a novel type II serine/threonine kinase receptor through interaction with the type I transforming growth factor-beta receptor. *J. Biol. Chem.* 270, 5625–5630 (1995); Liu, F., Ventura, F., Doody, J. & Massagué, J. Human type II receptor for bone morphogenic proteins (BMPs): extension of the two-kinase receptor model to the BMPs. *Mol. Cell. Biol.* 15, 3479–3486 (1995); Rosenzweig, B. L. et al. Cloning and characterization of a human type II receptor for bone morphogenetic proteins. *Proc. Natl. Acad. Sci. U.S.A.* 92, 7632–7636 (1995).

The nucleotide and amino acid sequence of BMPR2 are shown in SEQ ID NO:1 and SEQ ID NO:2, respectively, starting at nucleotide 1 and amino acid 1, respectively. However, the wild-type cDNA sequence for BMPR2 which is set forth in Genbank Accession No. NM_001204, assigns the adenosine of the initiation codon to position 409. Therefore, nucleotide position 1 used herein corresponds to nucleotide number 409 of the BMPR2 cDNA sequence set forth in Genbank Accession No. NM_001204. Thus, where a mutation is noted as being at, for example, nucleotide residue 1454, this corresponds to nucleotide residue 1862 of the sequence set forth in Genbank Accession No. NM_001204 (that is, 1454+408).

As used herein, a specific notation will be used to denote certain types of mutations. All notations referencing a nucleotide or amino acid residue will be understood to correspond to the residue number of the wild-type BMPR2 nucleic acid sequence set forth at SEQ ID NO:1, or of the wild-type BMPR-II polypeptide sequence set forth at SEQ ID NO:2. Thus, for example, the notation "T 367 C" will be used to indicate that the nucleotide T at position 367 of the sequence set forth at SEQ ID NO:1 has been replaced with a C. Similarly, the notation "355 del A" will be used to indicate that the nucleotide A at position 355 has been deleted. Furthermore, the notation 2408 ins TG" will be used to indicate that the nucleotides T and G, in that order, have been inserted following the nucleotide at position 2408.

In the method of the invention, the mutant BMPR-II polypeptide or mutated BMPR2 nucleic acid identified is associated with pulmonary hypertension.

In one embodiment, the subject having an increased susceptibility for developing pulmonary hypertension is identified by detecting a mutated BMPR2 nucleic acid in the subject. The mutated BMPR2 nucleic acid may comprise a missense mutation, that is, a mutation that changes a codon specific for one amino acid to a codon specific for another amino acid. As is noted below in the Examples and in Tables 1, 2, and 4, examples of mutated BMPR2 nucleic acids having a missense mutation which are associated with pulmonary hypertension include C 218 G, T 354 G, T 367 C, T 367 A, C 428 T, C 993 T, G 1042 A, T1258 C, A 1454 G, A 1535 C, T 1557 A, and C 2695 T.

In another embodiment, the BMPR2 nucleic acid having a sequence associated with pulmonary hypertension comprises a nucleic acid sequence having an insertion mutation, where one or more nucleotides are inserted into the wild-type sequence. The mutated BMPR2 nucleic acid may also comprise a deletion mutation, where one or more nucleotides are deleted from the wild-type sequence. Such a deletion or insertion mutation may, for example, result in a frameshift mutation, altering the reading frame. Frameshift mutations typically result in truncated (that is, prematurely terminated) BMPR-II polypeptide. As is noted below in the Examples and in Tables 1, 2, and 4, examples of BMPR2 nucleic acids having an insertion mutation which are associated with pulmonary hypertension include 504 ins T, 2292 ins A, and 2408 ins TG. Examples of BMPR2 nucleic acids having a deletion mutation which are associated with pulmonary hypertension include 355 del A, 689 del A, 958 del T, 1076 del C, 1191/1192 del TG, and 2579 del T.

The mutated BMPR2 nucleic acid may also comprise a nonsense mutation, that is, a mutation that changes a codon specific for an amino acid to a chain termination codon. Nonsense mutations result in truncated (that is, prematurely terminated) BMPR-II polypeptide. As is set forth below in the Examples and in Table 1, examples of BMPR2 nucleic acids having a nonsense mutation which are associated with pulmonary hypertension include C 218 G, C 428 T, C 993 T, and C 2695 T.

The mutated BMPR2 nucleic acid may also comprise a truncation mutation, that is, a mutated BMPR2 nucleic acid which encodes a truncated BMPR-II polypeptide. This may occur where, for example, the BMPR2 nucleic acid has a nonsense mutation.

In another embodiment, the mutated BMPR2 nucleic acid can be truncated at a nucleotide position of the sequence set forth in SEQ ID NO:1 which is 3' to nucleotide position 2695 of the sequence set forth at SEQ ID NO:1. As is set forth below in the Examples, it has been determined that a mutation at nucleotide 2695, which truncates the BMPR-II polypeptide at amino acid residue 899, is correlated to pulmonary hypertension.

In another embodiment, the mutated BMPR2 nucleic acid comprises a mutation at a nucleotide position of the sequence set forth in SEQ ID NO:1 selected from the group consisting of nucleotide 218, 354, 355, 367, 428, 504, 689, 958, 993, 1042, 1076, 1129, 1191, 1258, 1454, 1535, 1557, 1749, 2292, 2408, 2579, and 2695. The mutation can result in a change in a codon such that the mutated codon now encodes a different amino acid. The mutation can result in a polypeptide having a non-conservative substitution at the relevant amino acid residue. One of ordinary skill will readily understand the concept of a "non-conservative substitution." Substitutions such as a charged amino acid for an uncharged amino acid, or an uncharged amino acid for a charged amino acid, or any amino acid in place of a Cys, or visa versa, or any amino acid in place of a Pro, or visa versa, are well known in the art to alter the structure and often the function of a protein. The mutation can also result in reduction or elimination of BMPR2 mRNA production, incorrect or altered processing of BMPR2 RNA, increased BMPR2 RNA instability, or other effects on expression of BMPR2 prior to translation. For example, the mutation 1129 CG (Table 1) alters a splice junction and results in incorrect splicing of BMPR2 RNA. The mutation C 1749 T, which does not alter the encoded amino acid, likely affects RNA production, processing, or function.

In the embodiment wherein the mutation in the mutated BMPR2 nucleic acid results in a non-conservative substitution in the amino acid sequence encoded by the nucleic acid, the mutation in the mutated BMPR2 nucleic acid can be selected from the group consisting of C 218 G, T 354 G, T 367 C, T 367 A, C 428 T, C 993 T, G 1042 A, T1258 C, A 1454 G, A 1535 C, T 1557 A, C 2695 T. The non-conservative substitution may comprise at least one substitution at an amino acid position of the sequence set forth in SEQ ID NO:2 selected from the group consisting of: a Trp residue at amino acid position 118, an Arg residue at amino acid position 123, a Ser residue at amino acid position 123, a Leu residue at amino acid position 143, an Ile residue at amino acid position 348, an Arg residue at amino acid position 420, an Ala residue at amino acid position 485, a Gln residue at amino acid position Gln, and a Lys residue at amino acid position 519.

In yet another embodiment, the BMPR2 nucleic acid having a sequence associated with pulmonary hypertension encodes a mutant BMPR-II polypeptide.

For example, the mutant BMPR-II polypeptide having a sequence associated with pulmonary hypertension can comprise at least one mutation at an amino acid position of the sequence set forth in SEQ ID NO:2. Preferably, the BMPR-II polypeptide comprises at least one mutation at an amino acid position of the sequence set forth in SEQ ID NO:2 selected from the group consisting of 73, 118, 123, 143, 332, 348, 420, 485, 512, 519, and 899.

For example, the BMPR-II polypeptide acid having a sequence associated with pulmonary hypertension may comprise at least one mutation at an amino acid position of the sequence set forth in SEQ ID NO:2 selected from the group consisting of: a Trp residue at amino acid position 118, an Arg residue at amino acid position 123, a Ser residue at amino acid position 123, a Leu residue at amino acid position 143, an Ile residue at amino acid position 348, an Arg residue at amino acid position 420, an Ala residue at amino acid position 485, a Gln residue at amino acid position Gln, and a Lys residue at amino acid position 519.

In another embodiment, the BMPR-II polypeptide having a sequence associated with pulmonary hypertension terminates prematurely. In a preferred embodiment, the BMPR-II polypeptide having a sequence associated with pulmonary hypertension terminates at an amino acid position of the sequence set forth in SEQ ID NO:2 which is at or N-terminal to amino acid position 899, including amino acid positions 73, 332, and 899.

In another embodiment, the BMPR-II polypeptide having a sequence associated with pulmonary hypertension has a non-conservative amino acid substitution of at least one amino acid residue of a BMPR-II having the amino acid sequence set forth in SEQ ID NO:2.

In one embodiment, the non-conservative amino acid substitution comprises a non-conservative amino acid substitution of any of the following: at least one Cys residue of a BMPR-II having the amino acid sequence set forth in SEQ ID NO:2. In another embodiment, the non-conservative amino acid substitution comprises a non-conservative amino acid substitution of at least one Pro residue of a BMPR-II having the amino acid sequence set forth in SEQ ID NO:2. In another embodiment, the non-conservative amino acid substitution comprises a non-conservative amino acid substitution of at least one Lys residue of a BMPR-II having the amino acid sequence set forth in SEQ ID NO:2. In another embodiment, the non-conservative amino acid substitution comprises a non-conservative amino acid substitution of at least one Arg residue of a BMPR-II having the amino acid sequence set forth in SEQ ID NO:2. In another embodiment, the non-conservative amino acid substitution comprises a non-conservative amino acid substitution of at least one Asp residue of a BMPR-II having the amino acid sequence set forth in SEQ ID NO:2. In another embodiment, the non-conservative amino acid substitution comprises a non-conservative amino acid substitution of at least one Glu residue of a BMPR-II having the amino acid sequence set forth in SEQ ID NO:2.

The mutated BMPR2 nucleic acid and mutant BMPR-II polypeptide that is detected can be from any cause. For example, mutated BMPR2 nucleic acid can be the result of a familial mutation or a sporadic mutation.

Kits

The disclosed method is preferably carried out using a kit designed or adapted to detect one or more mutant BMPR-II polypeptides and/or one or more mutated BMPR2 nucleic acids. An example would be a kit for detecting a variety of mutated BMPR2 nucleic acids. Many such kits, and methods for using them are known.

Nucleic Acid Delivery

BMPR-II biological activity can be stimulated (or correct activity provided) in a subject by administering to the subject a nucleic acid encoding BMPR-II, using any method known for nucleic acid delivery into the cells of a subject. The BMPR2 nucleic acid is taken up by the cells of the subject and directs expression of the encoded BMPR-II in those cells that have taken up the nucleic acid. The BMPR2 nucleic acids of the present invention can be in the form of naked DNA or RNA, or the nucleic acids can be within a vector for delivering the nucleic acids to the cells. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPO-FECTAMINE (GIBCO-BRL, Inc., Gaithersburg, Md.), SUPERFECT (Qiagen, Inc. Hilden, Germany) and TRANS-FECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells a nucleic acid that encodes a BMPR-II polypeptide. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941–948, 1994), adeno-associated viral (AAV) vectors (Goodman et al., *Blood* 84:1492–1500, 1994), lentiviral vectors (Naidini et al., *Science* 272:263–267, 1996), pseudotyped retroviral vectors (Agrawal et al., *Exper. Hematol.* 24:738–747, 1996). Physical transduction techniques can also be used, such as liposome delivery and receptor-mediated and other endocytosis mechanisms (see, for example, Schwartzenberger et al., *Blood* 87:472–478, 1996). The present invention can be used in conjunction with any of these or other commonly used gene transfer methods.

In a particular example, to deliver a BMPR2 nucleic acid to the cells of a human subject in an adenovirus vector, the dosage can range from about $10^7$ to $10^9$ plaque forming unit (pfu) per injection but can be as high as $10^{12}$ pfu per injection (Crystal, *Hum. Gene Ther.* 8:985–1001, 1997; Alvarez and Curiel, *Hum. Gene Ther.* 8:597–613, 1997). Ideally, a subject will receive a single injection. If additional injections are necessary, they can be repeated at six month intervals for an indefinite period and/or until the efficacy of the treatment has been established.

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

Animal Models

Compounds identified as modulating BMPR2 or BMPR-II expression or proposed to affect PPH may be subsequently screened in any available animal model system, including, but not limited to, mice, rats, pigs, rabbits, and chickens (Smith, J D, *Lab. Anim. Sci.* 48:573–579, 1998; Narayanaswamy et al., *J. Vasc. Interv. Radiol.* 11:5–17, 2000; Poernama et al., *Aterioscler. Thromb.* 12:601–607, 1992; and Schreyer et al., *Aterioscler. Thromb.* 14:2053–2059, 1994). Test compounds are administered to these animals according to standard methods. Known animal models include monocrotalin injection, continuous air embolism, and fawn hooded rat. Some useful models are described by Johnson et al., Pulmonary veins and bronchial vessels undergo remodeling in sustained pulmonary hypertension induced by continuous air embolization into sheep, Experimental Lung Research. 23(5):459–73 (1997); Perkett et al., Expression of transforming growth factor-beta mRNAs and proteins in pulmonary vascular remodeling in the sheep air embolization model of pulmonary hypertension, American Journal of Respiratory Cell & Molecular Biology. 11(1):16–24 (1994); Perkett et al., Insulin-like growth factor I and pulmonary hypertension induced by continuous air embolization in sheep, American Journal of Respiratory Cell & Molecular Biology. 6(1):82–7 (1992); Perkett et al., Sequence of structural changes and elastin peptide release during vascular remodelling in sheep with chronic pulmonary hypertension induced by air embolization, American Journal of Pathology. 139(6):1319–32 (1991); Perkett et al., Continuous air embolization into sheep causes sustained pulmonary hypertension and increased pulmonary vasoreactivity, American Journal of Pathology. 132(3):444–54 (1988); Morio et al., Distal airspace enlargement in the fawn-hooded rat: influences of aging and alveolar wall destruction, Respiration. 68(1):78–86 (2001); Le Cras et al., Early abnormalities of pulmonary vascular development in the Fawn-Hooded rat raised at Denver's altitude, American Journal of Physiology—Lung Cellular & Molecular Physiology. 279(2):L283–91 (2000); Le Cras et al., Abnormal lung growth and the development of pulmonary hypertension in the Fawn-Hooded rat, American Journal of Physiology. 277(4 Pt 1):L709–18 (1999); Gonzalez et al., The pulmonary hypertensive fawn-hooded rat has a normal serotonin transporter coding sequence, American Journal of Respiratory Cell & Molecular Biology. 19(2):245–9 (1998); Gonzalez et al., Pulmonary hypertension, family and environment, Journal of Human Hypertension. 11(9):559–61 (1997); Provoost, Spontaneous glomerulosclerosis: insights from the fawn-hooded rat, Kidney International—Supplement. 45:S2–5 (1994); Sato et al., Factors influencing the idiopathic development of pulmonary hypertension in the fawn hooded rat, American Review of Respiratory Disease. 145(4 Pt 1):793–7 (1992); Ashmore et al., Paradoxical constriction to platelets by arteries from rats with pulmonary hypertension, American Journal of Physiology. 260(6 Pt 2):H1929–34 (1991); Nagaya et al., Gene transfer of human prostacyclin synthase ameliorates monocrotaline-induced pulmonary hypertension in rats, Circulation. 102 (16):2005–10 (2000); Shubat et al., Pulmonary vascular responses induced by the pyrrolizidine alkaloid, monocrotaline, in rats, Toxicon. 25(9):995–1002 (1987); Gust and Schuster, Vascular remodeling in experimentally induced subacute canine pulmonary hypertension, Experimental Lung Research. 27(1):1–12 (2001); Ito et al., Alterations of endothelium and smooth muscle function in monocrotaline-induced pulmonary hypertensive arteries, American Journal of Physiology—Heart & Circulatory Physiology. 279(4):H1786–95 (2000); Tanabe et al., Experimental study on monocrotaline induced pulmonary hypertensive rats. (1) Effect of long-term injection of immunosuppressant, Tokai Journal of Experimental & Clinical Medicine. 6(1):41–8 (1981); and Kameji et al., Increase of collagen synthesis in pulmonary arteries of monocrotaline-treated rats, Experientia. 36(4):441–2 (1980).

Animal models that mimic PPH can be developed using conventional molecular biology methods. For example, a transgenic animal (for example, a mouse) that overexpresses BMPR2 can be generated by inserting a BMPR2-encoding nucleic acid under the transcriptional regulation of the appropriate tissue-specific promoter into the genome of the animal.

Test Compounds

In general, novel drugs that modulate BMPR-II biological activity may be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (for example, semi-synthesis or total synthesis) of any number of chemical compounds, including, but not limited to, saccharide-, lipid-, peptide-, and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, for example, by standard extraction and fractionation methods. Furthermore, if desired, any library or compound is readily modified using standard chemical, physical, or biochemical methods.

In addition, those skilled in the art of drug discovery and development readily understand that methods for dereplication (for example, taxonomic dereplication, biological dereplication, and chemical dereplication, or any combination thereof) or the elimination of replicates or repeats of materials already known for their BMPR-II-modulatory activities should be employed whenever possible.

When a crude extract is found to modulate BMPR-II activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that mimics, stimulates, or antagonizes BMPR-II, depending upon the effect desired. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value can be subsequently analyzed using any animal models for PPH.

Administration of compounds that modulate BMPR-II biological activity

The compositions and methods described herein can be used therapeutically in combination with a pharmaceutically acceptable carrier. By "pharmaceutically acceptable carrier" is meant a material that is not biologically or otherwise undesirable, that is, the material may be administered to an individual along with a polypeptide, nucleic acid, or other compound of the invention without causing any undesirable biological effects or interacting in a deleterious manner with any of the components of the pharmaceutical composition in which it is contained. Pharmaceutical carriers are well-known in the art. These most typically are standard carriers for administration of vaccines or pharmaceuticals to humans, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like. Methods for making such formulations are well known in the art, and are described, for example, in: Remington: The Science and Practice of Pharmacy (19$^{th}$ ed.), ed. A. R. Gennaro, E. W. Martin Mack Publishing Co., Easton, Pa., 1995.

The pharmaceutical compositions may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The compounds and compositions of the present invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable. Formulations for parenteral administration may include sterile aqueous solutions which may also contain buffers, diluents and other suitable additives.

The compounds of the invention are administered in an effective amount, using standard approaches. Effective dosages and schedules for administering the compounds may be determined empirically, and making such determinations is routine to one of ordinary skill in the art. The skilled artisan will understand that the dosage will vary, depending upon, for example, the species of the subject the route of administration, the particular compound to be used, other drugs being administered, and the age, condition, sex and extent of the disease in the subject. The dosage can be adjusted by the individual physician in the event of any counterindications. A dose of a compound of the invention generally will range between about 1 µg/kg of body weight and 1 g/kg of body weight. Examples of such dosage ranges are, e.g., about 1 µg–100 µg/kg, 100 µg/kg–10 mg/kg, or 10 mg–1 g/kg, once a week, bi-weekly, daily, or two to four times daily. Compounds of the invention include BMPR-II polypeptides, BMPR2 nucleic acids, and molecules that regulate expression and/or biological activity of endogenous wild-type, polymorphic, and/or mutant BMPR-II polypeptides and/or nucleic acids (for example, DNA or RNA molecules) encoding such BMPR-II polypeptides.

The following Examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention.

EXAMPLES

Example 1

This example describes identification of BMPR2 mutations associated with susceptibility to PPH. To enable positional cloning of the FPPH gene (PPH1) a published YAC map was verified and extended at 2q33 to anchor a BAC/PAC contig including genomic sequences available at GenBank (Hadano, S. et al. A yeast artificial chromosome-based physical map of the juvenile amyotrophic lateral sclerosis (ALS2) critical region on human chromosome 2q33-q34. *Genomics* 55, 106–112 (1999)). This contig covers the entire 5.8 Mb PPH1 region defined by recently detected recombination events limited by the polymorphic STS markers D2S115 and D2S1384 (ref.12), and includes the nucleotide sequence encoding bone morphogenetic protein receptor type II (BMPR-II).

PCR primers were designed for amplification of patient genomic DNA after determination of the intron/exon boundaries of BMPR2. Sequence variants were identified from the panel of kindreds studied. Heterogeneous mutations, including frameshift, nonsense and missense mutations, were identified. These mutations were distributed across the gene.

Either restriction enzyme or sequence analysis of DNA from affected and unaffected first-degree relatives was used to show co-segregation of the mutations with the disease phenotype (including obligate gene carriers) in all but one of the pedigrees. 150 normal chromosomes derived from the same population as the affected families were screened together with a panel of 64 chromosomes from normal, but ethnically diverse, controls subjects. None of the mutations were detected in either panel.

Materials and Methods

Patients

We ascertained families in which at least two members had the typical manifestations of PPH after exclusion of known associated disorders, as previously described (5). We collected venous blood samples and extracted genomic DNA following informed consent. Obligate gene carriers are defined as those individuals who inherit and transmit the disease gene to an affected offspring but who themselves show no clinical manifestations of the disease.

Determination of the genomic structure of BMPR2

Available genomic sequence of BAC RP11-354N12 (http://www.ncbi.nlm.nih.gov/Genbank) was compared to the published cDNA sequence (Genbank Z48923) and the intron/exon boundaries for the 3' portion of the gene (exons 8–13) determined (14). To determine the intron/exon boundaries for exons 1–7, additional BAC clones were isolated by PCR screening of a human genomic BAC library (CITB B&C, Research Genetics) using both an exon 1 and exon 3 STS designed from the BMPR2 cDNA. Direct sequence analysis of the BAC clones with primer predicted to be near intron/exon junctions, based on the mouse Bmpr2 genomic structure, generated flanking intronic sequence for the remaining introns (18). Comparison between the human and published mouse genomic organization shows strong conservation of the intron/exon boundaries (18).

Mutational analysis

We screened the entire coding and intron/exon boundaries by direct sequencing of both forward and reverse strands on either an ABI 377 sequencer or an ABI 3700 DNA analyzer, using the Applied Biosystems DyeDeoxy or BigDye terminator kit and analysed the data using Sequence Analysis v3.2 or v3.6NT software (Perkin Elmer). The PCR primers for each exon were:

| | | |
|---|---|---|
| Exon1: | 5'-AGCTAGGTCCTCTCATCAGC-3' | (SEQ ID NO:3) |
| | 5'-CAGCCGCAGTGCTGACCAGC-3' | (SEQ ID NO:4); |
| Exon2: | 5'-GTCATTCGGATAAGACAAAG-3' | (SEQ ID NO:5) |
| | 5'-TTTAACATACTCCCATGTCC-3' | (SEQ ID NO:6); |

-continued

| | | |
|---|---|---|
| Exon3: | 5'-TAGCTTACACGTACTCTCAC-3' | (SEQ ID NO:7) |
| | 5'-CCTGGCTTCAACCTTGAATG-3' | (SEQ ID NO:8); |
| Exon4: | 5'-GGGTACAGCCTTTCTAAAGG-3' | (SEQ ID NO:9) |
| | 5'-GATACTATTGAGGCTGGGTG-3' | (SEQ ID NO:10); |
| Exon5: | 5'-GCTGCTAATCTTTCTGCAGC-3' | (SEQ ID NO:11) |
| | 5'-GAATGAAGTCACTGTTCCAG-3' | (SEQ ID NO:12); |
| Exon6: | 5'-CAGAGAGCTGTAGCATTCTG-3' | (SEQ ID NO:13) |
| | 5'-AAGTGATCCACCTGCCTTAG-3' | (SEQ ID NO:14); |
| Exon7: | 5'-ACTCTTCATGTTAAAGTGAG-3' | (SEQ ID NO:15) |
| | 5'-CTTTGAAGATATAATTAAAATTTCC-3' | (SEQ ID NO:16); |
| Exon8: | 5'-CACCTGGCCAGTAGATGTTT-3' | (SEQ ID NO:17) |
| | 5'TGTTCAATAGTCCCTTTTATTCATTG-3' | (SEQ ID NO:18); |
| Exon9: | 5'-CTAATTTGCATCCTGCTGCT-3' | (SEQ ID NO:19) |
| | 5'-TGTTCTTCAGAATATGCTACG TTCTC-3' | (SEQ ID NO:20); |
| Exon10: | 5'-TTGTGGCATTAGGCAACTCC-3' | (SEQ ID NO:21) |
| | 5'-GCCTGAAGGGGATGAA AAA-3' | (SEQ ID NO:22); |
| Exon11: | 5'-CCACACCCCTTAGGGTCTTA-3' | (SEQ ID NO:23) |
| | 5'-CACATGGTTTGACATGTAC TTTG-3' | (SEQ ID NO:24); |
| Exon12A: | 5'-CATCAGAGCTTTCCTTGAGGTT-3' | (SEQ ID NO:25) |
| | 5'-CAGAGGTGTTAAATTT GGAG-3' | (SEQ ID NO:26); |
| Exon12B: | 5'-TCTACCTGCCACACCATTCA-3' | (SEQ ID NO:27) |
| | 5'-TGGAAACCAACAAGCTAGACC-3' | (SEQ ID NO:28); |
| Exon12C: | 5'-CCCCAAAAGACACACAGGAG-3' | (SEQ ID NO:29) |
| | 5'-TGAATGGTGTGGCAGGTAGA-3' | (SEQ ID NO:30); |
| Exon13: | 5'-GCTGACAGGAGGATAAAGCA-3' | (SEQ ID NO:31) |
| | 5'-CACCCTCCTGAGACATTGGT-3' | (SEQ ID NO:32). |

Restriction endonuclease digestion

We confirmed segregation of the mutations within families and excluded the presence of the mutations in controls, including a panel from the DNA Polymorphism Discovery Resource, Coriell Cell Repositories, by PCR amplification of the relevant exon. This was followed by either mutation specific restriction fragment length polymorphism (RFLP) analysis or direct sequencing as previously described (23). Exon 12 (2579–2580delT) was PCR amplified using the following primers as a nested PCR reaction:5' ACCCAATATGCCAATGGGAC-3' (SEQ ID NO:33), 5'-TTCGCCACCTTCTAGTGGCT-3' (SEQ ID NO:34) followed by 5'-CATGTGGTAAACTGAAAAGCTCA-3' (SEQ ID NO:35), 5'-TTGAGACCACTTTGATACACACA-3' (SEQ ID NO:36). We digested an aliquot (10 μl) overnight at 37° C. with the appropriate enzyme (10 U; Gibco) and separated the fragments on a 4% agarose gel.

In keeping with the recognized reduced penetrance of FPPH, some individuals over 40 years of age exhibited the restriction fragments of a mutant but were not affected (individuals 6 and 10 in NL01). Nucleic acid mutations included A 1454 G (exon 11, AvaII, pedigree NL01), T 354 G (exon 3, Bsp1286I, pedigree US14), 2579–2580 delT (exon 12, AseI, pedigree US55), C 2695 T (exon 12, HaeIII, pedigree US33), 355 del A (exon 3, Bsp1286I, pedigree UK13), G 1042 A (exon 8, pedigree UK06), and C 218 G (exon 2, pedigreeUS35). Polypeptide mutations included D 485 G (pedigree NL01), C 118 W (pedigree US14), PTC+ 10aa (pedigree US55), R 899 X (pedigree US33), PTC+8aa (pedigree UK13), C 347 Y (pedigree UK06), and S 73 X (pedigree US35). The downstream amino acid position of the premature termination codon (PTC) is indicated by the designation "+Xaa" where X is number of amino acids downstream of the codon that is mutated. Sequence analysis of both forward and reverse strands was performed for those PPH families in which the observed mutation did not create or destroy a restriction site: G 1042 A (exon 8, pedigree UK06), and C 218 G (exon 2, pedigreeUS35).

Discussion

Members of the TGF-β superfamily transduce signals by binding to heteromeric complexes of type I and II receptors, activating serine/threonine kinases, leading to transcriptional regulation by phosphorylated Smads (Massagué, J. & Chen, Y-G. Controlling TGF-β signalling. *Genes Dev.* 14, 627–644 (2000)). In FPPH, mutations in the gene encoding BMPR-II lead to alterations in domains which have been identified in TGF-β type II receptors as being involved in ligand binding, kinase activity and heteromeric dimer formation (Wrana, J. L. et al. Two distinct transmembrane serine/threonine kinases from *Drosophila melanogaster* form an activin receptor complex. *Mol. Cell. Biol.* 14, 944–950 (1994); Carcamo, J., Zentella, A. & Massagué, J. Disruption of transforming growth factor beta signalling by a mutation that prevents transphosphorylation within the receptor complex. *Mol. Cell. Biol.* 15, 1573–1581 (1995); Gilboa, L. et al. Bone morphogenetic protein receptor complexes on the surface of live cells: A new oligomerization mode for serine/threonine kinase receptors. *Mol. Biol. Cell.* 11, 1023–1035 (2000)).

References

1. Rubin, L. ACCP consensus statement: primary pulmonary hypertension. *Chest* 104, 236–250 (1993).
2. Gaine, S. P. & Rubin, L. J. Primary pulmonary hypertension. *Lancet* 352, 719–725 (1998).
3. Rich, S. et al. Primary pulmonary hypertension: a national prospective study. *Ann. Intern. Med.* 107, 216–223 (1987).
4. Loyd, J. E., Primm, R. K. & Newman, J. H. Familial primary pulmonary hypertension: clinical patterns. *Am. Rev. Respir. Dis.*129, 194–197 (1984).
5. Nichols, W. C. et al. Localisation of the gene for familial primary pulmonary hypertension to chromosome 2q31–32. *Nature Genet.* 15, 277–280 (1997). Morse, J. H. et al. Mapping of familial pulmonary hypertension locus (PPH1) to chromosome 2q31–032. *Circulation* 95, 2603–2606 (1997).
7. Massagué, J. & Chen, Y-G. Controlling TGF-β signalling. *Genes Dev.* 14, 627–644 (2000).
8. Wrana, J. L. et al. Two distinct transmembrane serine/threonine kinases from *Drosophila melanogaster* form an activin receptor complex. *Mol. Cell. Biol.* 14, 944–950 (1994).
9. Carcamo, J., Zentella, A. & Massagué, J. Disruption of transforming growth factor beta signalling by a mutation that prevents transphosphorylation within the receptor complex. *Mol. Cell. Biol.* 15, 1573–1581 (1995).
10. Gilboa, L. et al. Bone morphogenetic protein receptor complexes on the surface of live cells: A new oligomerization mode for serine/threonine kinase receptors. *Mol. Biol. Cell.* 11, 1023–1035 (2000).
11. Hadano, S. et al. A yeast artificial chromosome-based physical map of the juvenile amyotrophic lateral sclerosis (ALS2) critical region on human chromosome 2q33-q34. *Genomics* 55, 106–112 (1999).
13. Kawabata, M., Chytil, A. & Moses, H. L. Cloning of a novel type II serine/threonine kinase receptor through interaction with the type I transforming growth factor-beta receptor. *J. Biol. Chem.* 270, 5625–5630 (1995).
14. Liu, F., Ventura, F., Doody, J. & Massagué, J. Human type II receptor for bone morphogenic proteins (BMPs): extension of the two-kinase receptor model to the BMPs. *Mol. C ell. Biol.* 15, 3479–3486 (1995).
15. Rosenzweig, B. L. et al. Cloning and characterization of a human type II receptor for bone morphogenetic proteins. *Proc. Natl. Acad. Sci. U.S.A.* 92, 7632–7636 (1995).
16. Botney, M. D., Bahadori, L. & Gold, L. I. Vascular remodeling in primary pulmonary hypertension. Potential role for transforming growth factor-beta. *Am. J. Pathol.* 144, 286–295 (1994).
17. Marchuk, D. A. Genetic abnormalities in hereditary hemorrhagic telangiectasia. *Curr. Opin. Hematol.* 5, 332–338 (1998).
18. Beppu, H., Minowa, O., Miyazono, K. & Kawabata, M. cDNA cloning and genomic organization of the mouse BMP type II receptor. *Biochem. Biophys. Res. Commun.* 235, 499–504 (1997).
19. Wilkie, A. O. The molecular basis of genetic dominance. *J. Med. Genet.* 31, 89–98 (1994).
21. Lu, S. L. et al. HNPCC associated with germline mutation in the TGF-beta type II receptor gene. *Nature Genet.* 19, 17–18 (1998).
22. Lee, S. D. et al. Monoclonal endothelial cell proliferation is present in primary but not secondary pulmonary hypertension. *J. Clin. Invest.* 101, 927–934 (1998). Shackleton, S. et al. *LMNA,* encoding lamin A/C, is mutated in partial lipodystrophy. *Nature Genet.* 24, 153–156 (2000).

Example 2

Materials and Methods

Patients

Patients (age range 14–55 years) were recruited through physicians at specialist pulmonary vascular clinics in the UK (n=35), France (n=13) and the USA (n=2). PPH was defined by standard clinical methods, including cardiac catheterization revealing pulmonary hypertension (mean pulmonary artery pressure>25 mm Hg) and a normal pulmonary artery wedge pressure, without other abnormalities such as lung disease, heart disease, pulmonary embolism or systemic disease such as connective tissue diseases. All studies were performed with consent and approval by the Leicestershire Health Authority Ethics Committee (England).

Typical Presentation

At age 36, patient 10 a previously fit and well nulliparous white female, developed shortness of breath and reduced exercise tolerance. She had no previous history of tobacco consumption, nor use of appetite suppressants. A five generation detailed pedigree revealed no preceding family history of PPH. The following year, she was investigated for worsening breathlessness. On clinical examination, external appearance was normal, cardiac auscultation revealed a loud second pulmonary heart sound. A radiograph of the chest showed enlarged pulmonary arteries with 'pruning' of peripheral vessels, electrocardiogram had evidence of right ventricular strain and an echocardiogram revealed an enlarged right ventricle and moderate tricuspid regurgitation. An autoantibody screen and ventilation/ perfusion scan were normal. At right heart catheterisation, pulmonary artery pressure was 97/41 mmHg with a pulmonary wedge pressure of 8 mmHg, and a diagnosis of primary pulmonary hypertension was made. The patient was anti-coagulated on warfarin and commenced on a calcium channel blocking agent, diltiazam. Her condition deteriorated over the following year with increasing episodes of retro-sternal chest pain, haemoptysis, syncope and the development of peripheral oedema. Domiciliary oxygen was provided and she was assessed for heart-lung transplantation, which she received at age 41. Histology of the explanted lungs showed marked intimal expansion and atheromatous plaques in the main branches of pulmonary arteries. Distal arteries showed hypertrophied muscularised media, intimal expansion and obliteration, with formation of plexiform lesions. The alveoli and bronchi appeared normal. A year following transplant she returned to work and remains under follow-up on a regime of immuno-suppression.

DNA Sequence Analysis of BMPR2 gene

We obtained 10 to 20 ml of peripheral blood from each family member studied. DNA was isolated from whole blood as described elsewhere. Parental relationships were confirmed through the segregation analysis of 10 independent highly polymorphic markers. Protein coding sequences from exons 1 to 13 were amplified from genomic DNA using primers derived from intron sequence as described in Example 1. Genomic fragments amplified by the polymerase chain reaction (PCR) were sequenced with a dye-terminator cycle-sequence system (ABI 3700, Perkin-Elmer Applied Biosystems, Foster City, Calif.).

Confirmation of Genotypes and Detection of Spontaneous (de novo) Mutations

Variants of the BMPR2 gene were identified by sequence analysis and, when possible, were independently confirmed by restriction endonuclease digestion. Relevant exons were PCR amplified using primers as described, digested with restriction enzymes (Hae III, Taq I, Mse I, Fnu4H I, New England Biolabs) according to the manufacturer's instructions, and size-separated on a 4% composite agarose gel (FMC BioProducts, Gibco BRL). The presence or absence of the sequence variants from available family members and at least 150 normal control chromosomes was determined by analysis of the restriction digest or direct sequencing results.

Results

Analysis of the BMPR2 Gene

Sequencing of genomic DNA of the panel of sporadic PPH subjects demonstrated a variety of novel heterozygous mutations of the BMPR2 gene (Table 4). In patients 1 and 2, the nucleotide sequence revealed substitutions of guanine for adenine in exons 2 and 3 respectively. These change the sequences of codon 60 from TGC to TAC (patient 1) and codon 117 from TGT to TAT (patient 2); both changing a highly conserved encoded amino acid from cysteine to tyrosine (Table 4). As these mutations do not result in either gain or loss of a restriction site, genomic sequencing of parental samples demonstrated the presence of the mutation in the fathers of both sporadic patients.

In patient 8, genomic sequencing identified a substitution of thymine for cytosine in exon 11, changing the sequence of codon 483 from TGT to CGT and the encoded amino acid from cysteine to arginine (Table 2). No additional family members were available for study. In patients 6 and 10, deletion of an adenine in exon 9 and a guanine in exon 12 both lead to a change in the coding reading frame, and predict premature truncation of the 1038 amino-acid protein at codon positions 423 and 803 respectively. Analysis of samples from unaffected parents, either by direct sequencing of genomic DNA (patient 6) or restriction enzyme analysis with Fnu4HI (patient 10), demonstrated the absence of the mutation, confirming these patients had spontaneous mutations of the BMPR2 gene (Table 4).

The possibility of incorrect paternity was excluded by the analysis of informative markers. The mutation observed in patient 10, was also detected in two further sporadic patients, 11 and 12 ascertained independently. No parental samples were available and the possibility of the patients having inherited the mutation from a common ancestor was excluded through the examination of genotypes from microsatellite markers from within and surrounding the BMPR2 gene on chromosome 2.

In three additional patients, insertions of residues in the genomic sequence occurred. In patient 4, an additional thymine was detected in exon 6 at position 787 (Table 4). In patient 7 both a guanine and adenine were inserted at nucleotide position 1247–8 of exon 9, while in patient 9 an adenine is inserted in exon 12 at position 1969 and confirmed through restriction digest analysis with Mse 1 (Table 4). Each of the mutations predicts premature truncation of the BMPR-II protein through shifts of the reading frame (Table 4). Parental material was not available for analysis for these subjects.

In patients 3 and 5, the substitution of cytosine for thymine occurred in exons 6 and 8 respectively (Table 4). In both patients the mutations result in the change of the encoded amino-acid arginine CGA to the stop signal TGA. These sequence changes were confirmed by restriction digest analysis of genomic DNA with HaeIII and TaqI respectively; however samples from other family members were not available.

None of these sequence changes were detected in the analysis of a large panel of chromosomes from unrelated normal individuals, indicating that these mutations are not polymorphisms. Mutations of the entire coding sequence of the BMPR2 gene were also excluded in the remaining 38 patients diagnosed with sporadic PPH.

Pulmonary artery myocytes from patients with familial and sporadic PPH exhibit abnormal responses to TGF-β family ligands PPH myocytes exhibited specifically heightened $^3$H-thymidine incorporation to BMP2, a known BMPR-II ligand, and TGF-β. In contrast, no increased DNA synthesis was observed in response to these peptides in cells from control subjects or patients with secondary pulmonary hypertension. Indeed, TGF-β suppressed basal $^3$H-thymidine incorporation in pulmonary artery myocytes from controls. PDGF-β stimulated $^3$H-thymidine incorporation by an equal amount in all cells, with no significant difference between patient groups. Growth arrested pulmonary artery myocytes from patients with PPH were used. Incubations were for 48 hours with [methyl]-$^3$H-thymidine added for final 24 hours. All subjects were age-matched and patients had a comparable degree of pulmonary hypertension: PPH (mean pulmonary artery pressure 604 mmHg); SPH (655 mmHg). *$p<0.05$, **$p<0.01$ compared with corresponding 0.1% FBS.

References

1. Rubin L J. Primary Pulmonary Hypertension. The New England Journal of Medicine 1997; 336:111–117.
2. Gaine S P, Rubin L J. Primary pulmonary hypertension. Lancet 1998; 352:719–725.
3. Rich S, Dantzker D R, Ayres S M, Bergofsky E H, Brundage B H, Detre K M, et al. Primary pulmonary hypertension. A national prospective study. Ann.Intern.Med. 1987; 107:216–223.
4. Loyd J E, Primm R K, Newman J H. Familial primary pulmonary hypertension: clinical patterns. Am.Rev-.Respir.Dis. 1984; 129:194–197.
5. Machado R D, Pauciulo M W, Fretwell N, Veal C, Thomson J R, Güell C V, et al. A physical and transcript map based upon refinement of the critical interval for PPH1, a gene for familial primary pulmonary hypertension. Genomics 2000; In press.
6. Nichols W C, Koller D L, Slovis B, Foroud T M, Terry V H, Arnold N D, et al. Localization of the gene for familial primary pulmonary hypertension to chromosome 2q31–32. Nat.Genet. 1997; 15:277–280.
7. Morse J H, Jones A C, Barst R J, Hodge S E, Wilhelmsen K C, Nygaard T G. Mapping of familial primary pulmonary hypertension locus (PPH1) to chromosome 2q31-q32. Circulation 1997; 95:2603–2606.
8. Deng Z, Haghighi F, Helleby L, Vanterpool K, Horn E M, Barst R J, et al. Fine mapping of PPH1, a gene for familial primary pulmonary hypertension, to a 3 cM region on chromosome 2q33. American Journal of Respiratory & Critical Care Medicine 2000; 161:1055–1059.
9. The International PPH Consortium, Lane K B, Machado R D, Pauciulo M W, Thomson J R, Phillips III J A, et al. Heterozygous germline mutations in a TGF-β receptor, BMPR2, are the cause of familial primary pulmonary hypertension. Nat.Genet. 2000; In press.
10. Massague J, Chen Y G. Controlling TGF-β signaling. Genes & Development 2000; 14:627–644.
11. Loyd J E, Atkinson J B, Pietra G G, Virmani R, Newman J H. Heterogeneity of Pathologic Lesions in Familial Primary Pulmonary Hypertension. Am.Rev.Respir.Dis. 1988; 138:952–957.
12. Pietra G G, Edwards W D, Kay J M, Rich S, Kernis J, Schloo B, et al. Histopathology of primary pulmonary hypertension. A qualitative and quantitative study of pulmonary blood vessels from 58 patients in the National Heart, Lung, and Blood Institute, Primary Pulmonary Hypertension Registry. Circulation 1989; 80:1198–1206.
13. Elliott G, Alexander G, Leppert M, Yeates S, Kerber R. Coancestry in apparently sporadic primary pulmonary hypertension. Chest 1995; 108:973–977.
14. Morrell N W, Upton P D, Kotecha S, Huntley A, Yacoub M H, Polak J M, et al. Angiotensin II activates MAPK and stimulates growth of human pulmonary artery smooth muscle via AT1 receptors. American Journal of Physiology 1999; 277:L1440–L448
15. Rich S. Primary pulmonary hypertension. Executive summary from the world symposium. Primary Pulmonary Hypertension. World Health Organisation Publications 1998;
16. Marchuk D A. Genetic abnormalities in hereditary hemorrhagic telangiectasia. Current Opinion in Hematology 1998; 5:332–338.
17. Blobe G C, Schiemann W P, Lodish H F. Role of transforming growth factor b in human disease. N Engl J Med 2000; 342:1350–1358.
18. Mesa R A, Edell E S, Dunn W F, Edwards W D. Human immunodeficiency virus infection and pulmonary hypertension: two new cases and a review of 86 reported cases. Mayo Clinic Proceedings 1998; 73:37–45.
19. Abenhaim L, Moride Y, Brenot F, Rich S, Benichou J, Kurz X, et al. Appetite-suppressant drugs and the risk of primary pulmonary hypertension. International Primary Pulmonary Hypertension Study Group [see comments]. N.Engl.J.Med. 1996; 335:609–616.
20. Gomez-Sanchez M A, Saenz d l C, Gomez-Pajuelo C, Martinez-Tello F J, Mestre d J M, James T N. Clinical and pathologic manifestations of pulmonary vascular disease in the toxic oil syndrome. Journal of the American College of Cardiology 1991; 18:1539–1545.
21. Lee S D, Shroyer K R, Markham N E, Cool C D, Voelkel N F, Tuder R M. Monoclonal endothelial cell proliferation is present in primary but not secondary pulmonary hypertension. Journal of Clinical Investigation 1998; 101:927–934.
22. Lu S L, Kawabata M, Imamura T, Akiyama Y, Nomizu T, Miyazono K, et al. HNPCC associated with gernline mutation in the TGF-β type II receptor gene. Nat.Genet. 1998; 19:17–18.

TABLE 1

| Family/Pt | Location | Mutation | Nucleotide change | Consequence | Segregation |
|---|---|---|---|---|---|
| +UK13 | Exon 3 | Deletion | 355delA GCTGTTGTA | frameshift | Bsp12861 |
| UK09 | Exon 3 | C123R | 367 TC | missense | MseI |
| UK21 | Exon 4 | Insertion | 504insT GTTGCCTTT | frameshift | |
| FRA | Exon 6 | Deletion | 689/90delAA TGCTGTAAA | frameshift | DS |
| +UK06 | Exon 8 | C347T | G1042A | missense | DS |
| GER01 | Exon 9 | C420R | T1258C | missense | AfaI/Bsp1407I/BsrGI/SspBI/MaeI |
| +NL01 | Exon 11 | D485G | A1454G | missense | AvaII |
| GRE01 | Exon 11 | L512T | A1535 C | missense | |
| SWE01 | Exon 12 | R584X | C1749T | nonsense | |
| UK22 | Exon 12 | Insertion | 2292insA ACCAAAAAA | frameshift | DS |
| UK11 | Exon 12 | Deletion | 2579–2580delT ATTAATT | frameshift (PTC + 10 aa) | AseI |
| UK04 | Exon 7 | Deletion | 958+3 delT AGGAGGTA | inactivates exon 7 donor splice site | |
| +US35 | Exon 2 | S73X | C218G | nonsense | DS |
| +US14 | Exon 3 | C118W | T354G | missense | Bsp12861 |
| +US33 | Exon 12 | R899X | C2695T | nonsense | HaeIII |
| +US55 | Exon 12 | Deletion | 2579–2580delT ATTAATT | frameshift (PTC + 10 aa) | AseI |
| US94 | Exon8 | Deletion | 1076delC GGCTGAC | frameshift (PTC + 15 aa) | |
| US89 | Exon 9 | Deletion | 1191/1192delTG GGACTGTG | frameshift (PTC + 48 aa) | |
| US80 | Exon 9 | Splice Defect | 1129-3CG | inactivates exon 9 acceptor splice site | |
| US37 | Exon 4 | R147X | C428T | nonsense | |
| US49 | Exon 11 | N519K | T1557A | missense | DS |
| US79 | Exon 12 | Insertion | 2408insTG TGGTGTG | frameshift (PTC + 3 aa) | |
| NOR01 | Exon 3 | C123S | T367A | missense | MseI |
| US50 | Exon 8 | R332X | C993T | nonsense | |

TABLE 2

| Patient | Location | Mutation | Nucleotide change | Consequence | Segregation | Mat | Pat | Centre |
|---|---|---|---|---|---|---|---|---|
| 5226 | Exon 2 | C60Y | G179A | missense | DS | WT | C196Y | Manchester |
| 3576 | Exon 6 | Insertion | TTTATAGTTT | frameshift | DS | Declined | Declined | Newcastle |
| 5949 | Exon 6 | R211x | C631T | nonsense | HaeIII | Alive, sample being arranged | Alive, sample being arranged | France |
| 5591 | Exon 8 | R332X | C994T | nonsense | TaqI | Alive, to arrange sample | Alive, to arrange sample | CXH |

TABLE 2-continued

| Patient | Location | Mutation | Nucleotide change | Consequence | Segregation | Mat | Pat | Centre |
|---|---|---|---|---|---|---|---|---|
| 5508 | Exon 9 | Insertion | GGGAGAGA 1247/48insGA | frameshift | DS | Alive, to arrange sample | ? | Glasgow |
| 5927 | Exon 11 | C483R | T1447C | missense | DS | Blood sample taken | ? | France |
| 5545 | Exon 12 | Insertion | TCTGCTTAA 1969insA | frameshift | MseI | WT | RIP | Newcastle |
| 5163 | Exon 12 | Deletion | CAATCAATG 2386delG | frameshift | Fnu4HI | WT | WT | Harefield |
| 5937 | Exon 12 | Deletion | CAATCAATG 2386delG | frameshift | Fnu4HI | To request | To request | France |
| 5943 | Exon 12 | Deletion | CAATCAATG 2386delG | frameshift | Fnu4HI | To request | To request | France |
| Ut. 01 | Exon 9 | Deletion | GGGAGATA 1248delA | frameshift | DS | WT | WT | Utah |
| Ut. 11 | Exon 3 | C117Y | 350G--A | missense | DS | WT | C117Y | Utah |

TABLE 3

Clinical features of PPH.

| Characteristics | 1 | 2 | 3 | 4 | 5 | 6 | 7 | 8 | 9 | 10 | 11 | 12 |
|---|---|---|---|---|---|---|---|---|---|---|---|---|
| Sex | F | M | F | F | F | M | M | F | F | F | F | M |
| Age (years) | 23 | 31 | | 27 | 35 | 29 | 42 | | 34 | 43 | | |
| Age of onset (years) | 17 | 25 | | 22 | 29 | 22 | | | 30 | 36 | | |
| Family History | − | − | − | − | − | − | − | − | − | − | − | − |
| Therapy (vasodilators) | + | + | + | + | + | − | + | + | + | − | + | + |
| HLT | − | − | − | − | − | + | − | − | − | + | − | − |
| Mutation BMPR2 | C60Y | C117Y | R211X | 787insT | R332X | 1248-delA | 1247/48-insGA | C483R | 1969-insA | 2386-delG | 2386-delG | 2386-delG |

TABLE 4

Mutations identified.

| Patient No. | Patient Identifier | Exon | Mutation Type | Nucleotide Change | Codon Position | Amino Acid Change | Inheritance | Restriction Enzyme |
|---|---|---|---|---|---|---|---|---|
| 1 | 5226 | 2 | Missense | G(179) A | 60 | Cys to Tyr | Paternal | — |
| 2 | Ut.11 | 3 | Missense | G(350) A | 117 | Cys to Tyr | Paternal | — |
| 3 | 3576 | 6 | Frameshift | 787insT | 263 | $PTC^{+3}$ | — | — |
| 4 | 5949 | 6 | Nonsense | C(631) T | 211 | Arg to Stop | — | HaeIII |
| 5 | 5591 | 8 | Nonsense | C(994) T | 332 | Arg to Stop | — | TaqI |
| 6 | Ut.01 | 9 | Frameshift | 1248delA | 416 | $PTC^{+7}$ | de novo | — |
| 7 | 5508 | 9 | Frameshift | 1247/8ins GA | 416 | $PTC^{+4}$ | — | — |
| 8 | 5927 | 11 | Missense | T(1447) C | 483 | Cys to Arg | — | — |
| 9 | 5545 | 12 | Frameshift | 1969insA | 657 | $PTC^{+18}$ | — | MseI |
| 10 | 5163 | 12 | Frameshift | 2386delG | 796 | $PTC^{+7}$ | de novo | Fnu4HI |
| 11 | 5937 | 12 | Frameshift | 2386delG | 796 | $PTC^{+7}$ | — | Fnu4HI |
| 12 | 5943 | 12 | Frameshift | 2386delG | 796 | $PTC^{+7}$ | — | Fnu4HI |
| 13 | 5597 | 1–6 | Deletion | | | | | |

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method of identifying a subject having an increased susceptibility for developing pulmonary hypertension, comprising detecting a mutated Bone Morphogenic Protein Receptor 2 (BMPR2) nucleic acid in the subject, thereby identifying a subject having an increased susceptibility for developing pulmonary hypertension,
wherein the mutated BMPR2 nucleic acid has a sequence associated with pulmonary hypertension, wherein the mutated BMPR2 nucleic acid comprises a mutation at a nucleotide position of the sequence set forth in SEQ ID NO:1 selected from the group consisting of 218, 354, 367, 428, 1258, 1454, 1535, and 1557,
wherein the mutation in the mutated BMPR2 nucleic acid results in a non-conservative substitution in the amino acid sequence encoded by the nucleic acid, wherein the mutation is selected from the group consisting of C 218 G, T 354 G, T 367 C, T 367 A, C 428 T, T 1258 C, A 1454 G, A 1535 C, and T 1557 A.

2. A method of identifying a subject having an increased susceptibility for developing pulmonary hypertension, comprising detecting a mutated Bone Morphogenic Protein Receptor 2 (BMPR2) nucleic acid in the subject, thereby identifying a subject having an increased susceptibility for developing pulmonary hypertension,
wherein the subject having an increased susceptibility for developing pulmonary hypertension is identified by detecting a BMPR2 nucleic acid having a sequence associated with pulmonary hypertension, wherein the BMPR2 nucleic acid having a sequence associated with pulmonary hypertension encodes a mutant BMPR-II polypeptide,
wherein the BMPR-II polypeptide comprises at least one mutation at an amino acid position of the sequence set forth in SEQ ID NO:2 selected from the group consisting of a Trp residue at amino acid position 118, an Arg residue at amino acid position 123, a Ser residue at amino acid position 123, a Leu residue at amino acid position 143, an Arg residue at amino acid position 420, an Ala residue at amino acid position 485, a Gln residue at amino acid position Gln, and a Lys residue at amino acid position 519.

3. A method of identifying a subject having an increased susceptibility for developing pulmonary hypertension, comprising detecting a mutated Bone Morphogenic Protein Receptor 2 (BMPR2) nucleic acid in the subject, thereby identifying a subject having an increased susceptibility for developing pulmonary hypertension, wherein the mutated BMPR2 nucleic acid comprises a mutation selected from the group consisting of C 218 G, T 354 G, T 367 C, T 367 A, C 428 T, T 1258 C, A 1454 G, A 1535 C, and T 1557 A.

4. A method of identifying a subject having an increased susceptibility for developing pulmonary hypertension, comprising detecting a mutated Bone Morphogenic Protein Receptor 2 (BMPR2) nucleic acid in the subject, thereby identifying a subject having an increased susceptibility for developing pulmonary hypertension, wherein the BMPR2 nucleic acid encodes a mutant BMPR-II polypeptide, wherein the BMPR-II polypeptide comprises at least one mutation selected from the group consisting of a Trp residue at amino acid position 118, an Arg residue at amino acid position 123, a Ser residue at amino acid position 123, a Leu residue at amino acid position 143, an Arg residue at amino acid position 420, an Ala residue at amino acid position 485, a Gln residue at amino acid position Gln, and a Lys residue at amino acid position 519.

* * * * *